US009060722B2

(12) United States Patent
Teixeira

(10) Patent No.: US 9,060,722 B2
(45) Date of Patent: Jun. 23, 2015

(54) APPARATUS FOR PROCESSING PHYSIOLOGICAL SENSOR DATA USING A PHYSIOLOGICAL MODEL AND METHOD OF OPERATION THEREFOR

(76) Inventor: Rodrigo E. Teixeira, Madison, AL (US)

(*) Notice: Subject to any disclaimer, the term of this patent is extended or adjusted under 35 U.S.C. 154(b) by 717 days.

(21) Appl. No.: 12/796,512

(22) Filed: Jun. 8, 2010

(65) Prior Publication Data

US 2011/0301436 A1    Dec. 8, 2011

(51) Int. Cl.
*A61B 5/00* (2006.01)
*A61B 5/1455* (2006.01)
*A61B 5/0402* (2006.01)

(52) U.S. Cl.
CPC ........... *A61B 5/14552* (2013.01); *A61B 5/0402* (2013.01); *A61B 5/7267* (2013.01)

(58) Field of Classification Search
CPC .......................... A61B 5/0402; A61B 5/14552
See application file for complete search history.

(56) References Cited

U.S. PATENT DOCUMENTS

| 4,802,486 | A | 2/1989 | Goodman et al. | |
|---|---|---|---|---|
| 5,626,140 | A * | 5/1997 | Feldman et al. | 600/484 |
| 5,853,364 | A | 12/1998 | Baker | |
| 6,463,311 | B1 | 10/2002 | Diab | |
| 6,511,436 | B1 * | 1/2003 | Asmar | 600/500 |
| 7,018,338 | B2 * | 3/2006 | Vetter et al. | 600/503 |
| 7,020,507 | B2 | 3/2006 | Scharf | |
| 7,079,888 | B2 | 7/2006 | Oung et al. | |
| 7,149,320 | B2 | 12/2006 | Haykin | |
| 7,460,915 | B2 * | 12/2008 | Marik et al. | 700/31 |
| 8,494,829 | B2 | 7/2013 | Teixeira | |
| 2004/0122703 | A1 | 6/2004 | Walker et al. | |
| 2004/0171950 | A1 | 9/2004 | Starr et al. | |
| 2005/0113703 | A1 * | 5/2005 | Farringdon et al. | 600/509 |
| 2005/0143634 | A1 | 6/2005 | Baker et al. | |
| 2007/0100213 | A1 * | 5/2007 | Dossas et al. | 600/300 |
| 2008/0027341 | A1 | 1/2008 | Sackner | |
| 2008/0082018 | A1 | 4/2008 | Sackner et al. | |
| 2009/0024332 | A1 | 1/2009 | Karlov | |
| 2009/0069647 | A1 | 3/2009 | McNames | |
| 2010/0228102 | A1 | 9/2010 | Addison et al. | |
| 2010/0274102 | A1 | 10/2010 | Teixeira | |
| 2011/0077484 | A1 * | 3/2011 | Van Slyke et al. | 600/324 |
| 2011/0301436 | A1 | 12/2011 | Teixeira | |
| 2012/0022336 | A1 | 1/2012 | Teixeira | |
| 2012/0022350 | A1 | 1/2012 | Teixeira | |

(Continued)

FOREIGN PATENT DOCUMENTS

WO    WO 2008/055173 A2    5/2008

OTHER PUBLICATIONS

Arulampalam et al. IEEE Transactions on Signal Processing, Vol. 50, No. 2, 2002, 174-187.

(Continued)

*Primary Examiner* — Michael Kahelin
*Assistant Examiner* — Mitchell E Alter
(74) *Attorney, Agent, or Firm* — Kevin Hazen

(57) ABSTRACT

A pulse oximeter system comprises a data processor configured to perform a method that combines a sigma point Kalman filter (SPKF) or sequential Monte Carlo (SMC) algorithm with Bayesian statistics and a mathematical model comprising a cardiovascular model and a plethysmography model to remove contaminating noise and artifacts from the pulse oximeter sensor output and measure blood oxygen saturation, heart rate, left-ventricular stroke volume, aortic pressure and systemic pressures.

6 Claims, 16 Drawing Sheets

(56) References Cited

U.S. PATENT DOCUMENTS

| | | |
|---|---|---|
| 2012/0022384 A1 | 1/2012 | Teixeira |
| 2012/0022805 A1 | 1/2012 | Teixeira |
| 2012/0022844 A1 | 1/2012 | Teixeira |
| 2012/0277545 A1 | 11/2012 | Teixeira |
| 2014/0275886 A1 | 9/2014 | Teixeira |

OTHER PUBLICATIONS

Singer et al. Pub Med PMID:3063772, abstract ( J Electrocardiol. 1988;21 Suppl:S46-S55).

Wukitsch et al., Journal of Clinical Monitoring, vol. 4, pp. 290-301, 1998.

* cited by examiner

APPARATUS FOR PROCESSING PHYSIOLOGICAL SENSOR DATA USING A PHYSIOLOGICAL MODEL AND METHOD OF OPERATION THEREFOR

STATEMENT REGARDING FEDERALLY SPONSORED RESEARCH OR DEVELOPMENT

The U.S. Government may have certain rights to this invention pursuant to Contract Number IIP-0839734 awarded by the National Science Foundation.

CROSS-REFERENCES TO RELATED APPLICATIONS

This application claims priority to U.S. patent application Ser. No. 12/640,278, filed Dec. 17, 2009, which under 25 U.S.C. 120 claims benefit of U.S. provisional patent application No. 61/171,802, filed Apr. 22, 2009, which are incorporated herein in their entirety by this reference thereto.

BACKGROUND OF THE INVENTION

1. Field of the Invention

The present invention relates generally to apparatus and methods for processing physiological sensor data.

2. Discussion of the Related Art

Biomedical monitoring devices such as pulse oximeters, glucose sensors, electrocardiograms, capnometers, fetal monitors, electromyograms, electroencephalograms, and ultrasounds are sensitive to noise and artifacts. Typical sources of noise and artifacts include baseline wander, electrode-motion artifacts, physiological artifacts, high-frequency noise, and external interference. Some artifacts can resemble real processes, such as ectopic beats, and cannot be removed reliably by simple filters; however, these are removable by the techniques taught herein.

Patents related to the current invention are summarized herein.

Lung Volume

M. Sackner, et. al. "Systems and Methods for Respiratory Event Detection", U.S. patent application no. 2008/0082018 (Apr. 3, 2008) describe a system and method of processing respiratory signals from inductive plethysmographic sensors in an ambulatory setting that filters for artifact rejection to improve calibration of sensor data and to produce output indicative of lung volume.

Pulse Oximeter

J. Scharf, et. al. "Separating Motion from Cardiac Signals Using Second Order Derivative of the Photo-Plethysmograph and Fast Fourier Transforms", U.S. Pat. No. 7,020,507 (Mar. 28, 2006) describes the use of filtering photo-plethysmograph data in the time domain to remove motion artifacts.

M. Diab, et. al. "Plethysmograph Pulse Recognition Processor", U.S. Pat. No. 6,463,311 (Oct. 8, 2002) describe an intelligent, rule-based processor for recognition of individual pulses in a pulse oximeter-derived photo-plethysmograph waveform operating using a first phase to detect candidate pulses and a second phase applying a plethysmograph model to the candidate pulses resulting in period and signal strength of each pulse along with pulse density.

C. Baker, et. al. "Method and Apparatus for Estimating Physiological Parameters Using Model-Based Adaptive Filtering", U.S. Pat. No. 5,853,364 (Dec. 29, 1998) describe a method and apparatus for processing pulse oximeter data taking into account physical limitations using mathematical models to estimate physiological parameters.

Cardiac

J. McNames, et. al. "Method, System, and Apparatus for Cardiovascular Signal Analysis, Modeling, and Monitoring", U.S. patent application publication no. 2009/0069647 (Mar. 12, 2009) describe a method and apparatus to monitor arterial blood pressure, pulse oximetry, and intracranial pressure to yield heart rate, respiratory rate, and pulse pressure variation using a statistical state-space model of cardiovascular signals and a generalized Kalman filter to simultaneously estimate and track the cardiovascular parameters of interest.

M. Sackner, et. al. "Method and System for Extracting Cardiac Parameters from Plethysmograph Signals", U.S. patent application publication no. 2008/0027341 (Jan. 31, 2008) describe a method and system for extracting cardiac parameters from ambulatory plethysmographic signal to determine ventricular wall motion.

Hemorrhage

P. Cox, et. al. "Methods and Systems for Non-Invasive Internal Hemorrhage Detection", International Publication no. WO 2008/055173 A2 (May 8, 2008) describe a method and system for detecting internal hemorrhaging using a probabilistic network operating on data from an electrocardiogram, a photoplethysmogram, and oxygen, respiratory, skin temperature, and blood pressure measurements to determine if the person has internal hemorrhaging.

Disease Detection

V. Karlov, et. al. "Diagnosing Inapparent Diseases From Common Clinical Tests Using Bayesian Analysis", U.S. patent application publication no. 2009/0024332 (Jan. 22, 2009) describe a system and method of diagnosing or screening for diseases using a Bayesian probability estimation technique on a database of clinical data.

Statement of the Problem

The influence of multiple sources of contaminating signals often overlaps the frequency of the signal of interest, making it difficult, if not impossible, to apply conventional filtering. Severe artifacts such as occasional signal dropouts due to sensor movement or large periodic artifacts are also difficult to filter in real time. Biological sensor hardware can be equipped with a computer comprising software for post-processing data and reducing or rejecting noise and artifacts. Current filtering techniques typically use some knowledge of the expected frequencies of interest where the sought-after physiological information should be found, and do not contain a mathematical model describing either the physiological processes that are measured or the physical processes that measure the signal.

Adaptive filtering has been used to attenuate artifacts in pulse oximeter signals corrupted with overlapping frequency noise bands by estimating the magnitude of noise caused by patient motion and other artifacts, and canceling its contribution from pulse oximeter signals during patient movement. Such a time correlation method relies on a series of assumptions and approximations to the expected signal, noise, and artifact spectra, which compromises accuracy, reliability and general applicability.

Biomedical filtering techniques based on Kalman and extended Kalman techniques offer advantages over conventional methods and work well for filtering linear systems or systems with small nonlinearities and Gaussian noise. These filters, however, are not adequate for filtering highly nonlinear systems and non-Gaussian/non-stationary noise. Therefore, obtaining reliable biomedical signals continue to present problems, particularly when measurements are made in mobile, ambulatory, and physically active patients.

Existing data processing techniques, including adaptive noise cancellation filters, are unable to extract information that is hidden or embedded in biomedical signals and also discard some potentially valuable information.

SUMMARY OF THE INVENTION

The invention comprises use of a probabilistic model to extract physiological information from a biomedical sensor.

DETAILED DESCRIPTION OF THE INVENTION

Figure 1:
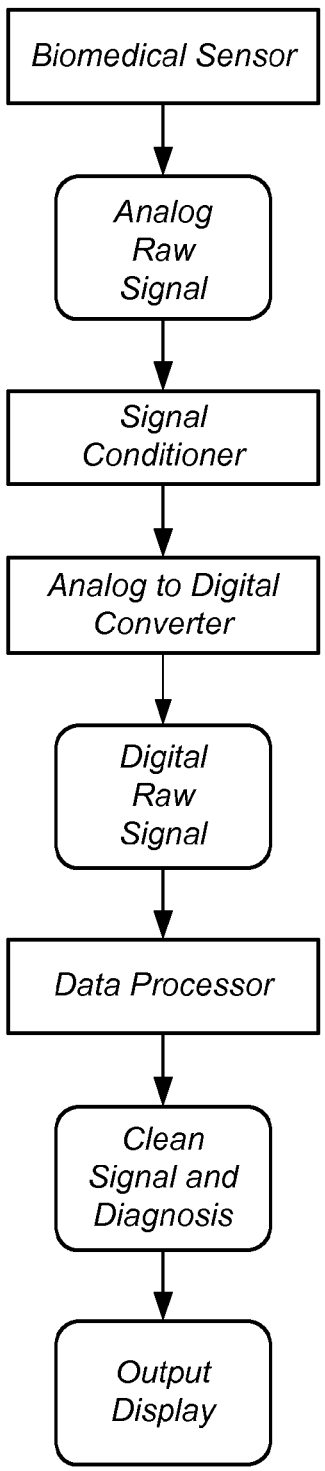
FIG. 1 is a flow chart showing the path of information flow from a biomedical sensor to a data a processor and on to an output display according to one embodiment of the invention.

The invention comprises use of a method, system, and/or apparatus using a probabilistic model to extract physiological information from a biomedical sensor.

In one embodiment, the system relates generally to apparatus and methods for processing physiological sensor data, such as pulse oximeter data. A data processing system associated with the pulse oximeter improves the accuracy of blood oxygen saturation and heart rate measurements made by the pulse oximeter and is used to estimate physiological conditions, such as stroke volume, cardiac output, and other cardiovascular and respiratory parameters.

In one embodiment, the system fills a need in the art for biomedical monitoring devices capable of accurately and reliably measuring physiological parameters made in mobile, ambulatory, and physically active patients. For instance, pulse oximeters are currently used to measure blood oxygen saturation and heart rate. A pulse oximetry signal, however, carries additional information that is extracted using the present invention to estimate additional physiological parameters including left-ventricular stroke volume, aortic blood pressure, and systemic blood pressure.

In another embodiment, a pulse oximeter system comprising a data processor configured to perform a method combines a sigma point Kalman filter (SPKF) or sequential Monte Carlo (SMC) algorithm with Bayesian statistics and a mathematical model comprising a cardiovascular model and a plethysmography model to remove contaminating noise and artifacts from the pulse oximeter sensor output to measure blood oxygen saturation, heart rate, left-ventricular stroke volume, aortic blood pressure, systemic blood pressure, and total blood volume.

In yet another embodiment described herein, an electrocardiograph (ECG) comprising a data processor configured to perform a method combines a sigma point Kalman filter (SPKF) or sequential Monte Carlo (SMC) algorithm with Bayesian statistics and a mathematical model comprising a cardiovascular model including heart electrodynamics, electronic/contractile wave propagation and a model to remove contaminating noise and artifacts from electrode leads and sensor output to produce electrocardiograms.

In various embodiments, the combination of SPKF or SMC in state, joint or dual estimation modes is optionally used to filter output from any biomedical device using appropriate physical models of the body, which are optionally chemical, electrical, optical, mechanical, or fluid based models.

The computational model includes variable state parameter output data that corresponds to a physiological parameter being measured to mathematically represent a current physiological state for a subject. The physiological parameter being measured is, most preferably, directly represented by a variable state parameter such that the value for the state parameter at time t is equal to an estimated value for the physiological parameter at time t. The estimated value of the physiological parameter being measured (estimated) also corresponds directly to (i.e. is about equal to) the value of the model parameter at time t or the estimated value for the physiological parameter is optionally calculated from a state parameter, a model parameter, or a combination of one or more state and/or model parameters.

Sigma Point Kalman Filter

Herein, a sigma point Kalman filter (SPKF) refers a filter using a set of weighted sigma-points that are deterministically calculated, such as by using the mean and square-root decomposition, or an equivalent, of the covariance matrix of a prior to about capture or completely capture at least the first and second order moments of the prior. The sigma-points are subsequently propagated in time through a dynamic state-space model (DSSM) to generate a posterior sigma-point set. Then, posterior statistics are calculated using tractable functions of the propagated sigma-points and weights, and new measurement.

Sigma point Kalman filters advantages and disadvantages are described herein. A sigma point Kalman filter interprets a noisy measurement in the context of a mathematical model describing the system and measurement dynamics. This gives the SPKF inherent superior performance to all "model-less" methods such as Wiener filtering, wavelet de-noising, principal component analysis, independent component analysis, nonlinear projective filtering, clustering methods, and many others.

A sigma point Kalman filter is superior to the basic Kalman filter, extended Kalman filter, and related variants of the Kalman filters, the sigma point Kalman filter yields higher accuracy with equal algorithm complexity, while also being easier to implement in practice. Conversely, the extended Kalman filter propagates the random variable using a single measure, usually the mean, and a first order Taylor expansion of the nonlinear DSSM. A sigma point Kalman filter, on the other hand, decomposes the random variable into distribution moments and propagates those using the unmodified nonlinear DSSM.

Sequential Monte Carlo

Sequential Monte Carlo (SMC) methods approximate the prior through use of a set of weighted samples without making assumptions about its form. The samples are then propagated in time through the unmodified DSSM. The resulting samples are used to update the posterior via Bayes rule and the latest noisy measurement.

SPKF and SMC

In general, sequential Monte Carlo methods have analysis advantages compared to the sigma point Kalman filters, but are more computationally expensive. However, the SPKF uses a sigma-point set, which is an exact representation only for Gaussian probability distribution functions (PDFs). As a result, SPKFs lose accuracy when PDFs depart heavily from the Gaussian form, such as with bimodal, heavily-tailed, or nonstationary distributions. Hence, both the SMC and SPKF filters have advantages. However, either a SMC or SPKF is used to propagate the prior using the unmodified DSSM. Examples herein are non-limiting; when a SMC filter is used an SPKF filter is optionally used and vise-versa.

SPKF or SMC is used to generate a reference signal in the form of a first probability distribution from the model's current (time=t) physiological state. The reference signal probability distribution and a probability distribution generated from a measured signal from a sensor at a subsequent time (time=t+n) are convoluted using Bayesian statistics to estimate the true value of the measured physiological parameter at time=t+n. The probability distribution function is optionally discrete or continuous, and is optionally used to identify the probability of each value of an unidentified random variable (discrete), or the probability of the value falling within a particular interval (continuous).

An example is provided to aid a subsequent detailed description of the probabilistic model system. Noise results from movement of a sensor. For an ambulatory patient, movement results from a bump in the road in an ambulance ride or simply movement of a sensor resultant from movement of the patient. Mathematically, artifacts and/or signal dropouts are simply noise with non-stationary PDFs. The probabilistic model is particularly resistant to these noise, motion, and artifact events because it does not assume noise is stationary and therefore will treat artifacts and dropouts the same as noise. As a result, measurements that do not correspond to the system dynamics human physiology described in the DSSM are assigned low probabilities and are essentially ignored by the model. Further, the system allows use of additional inputs such as accelerometer data. The accelerometer data and a sensor motion model is used to further inform the model when artificial noise is present in a fusion of models system. An example illustrates.

For example, patient movement during transport, when ambulatory, or even laying on the recovery bed, imparts acceleration forces that perturb the sensor and register as artifact, or even result in temporary signal dropout or loss. These movement or motion artifacts can be introduced, for instance, by altering the sensor-skin contact pressure, stretching the skin, or displacing the sensor. However, movement may also have real physiological effects such as organ compression and hemodynamic alterations. An accelerometer, gyroscope, or any data stream with movement information may be used to counter the unwanted effects of movement. That is, movement data can be used as inputs to a model that describes the effect of movement on measurement. Then, by extending the DSSM with this model, data from biomedical sensors and motion sensors are optionally fused, resulting in a cancellation of the unwanted effects of motion. Unlike conventional methods, this approach does not require spectral separation between wanted and unwanted frequencies.

Referring now to FIG. 1, an example of a top-level schematic for data processing is provided. A biomedical sensor, usually associated with a biomedical monitoring device, normally produces a raw analog output signal that is converted to a raw digital output signal. The analog to digital conversion is optionally used in combination with signal filtering or conditioning. Digital signals are received by a data processor configured to process the digital data and produce a processed (or clean) signal comprising an estimated true value for the physiological parameter being measured. The processed signal is then hard displayed, for example, in the form of an electronic, hard copy, audible, visual, and/or tactile output. The output is optionally used, for example, by a user to monitor a patient, by a user for self monitoring, or by a user as biofeedback process.

Still referring to FIG. 1, The data processor shown is configured to receive, as input data, digital signals from one or more biomedical sensors, and enter the data into a dynamic state-space model (DSSM) integrated with a processor engine. The integrated dynamic state-space model/processor engine produces transformed output data that corresponds to a physiological parameter measured by the biomedical sensor(s), in the form of an estimated true value for the physiological parameter. The processor engine optionally operates in a dual estimation mode (a dual estimation engine) or in a joint estimation mode (a joint estimation engine). The output optionally includes additional outputs corresponding to physiological parameters not measured by the physiological sensor(s), diagnostic information, and a confidence interval representing the probability that the output estimated value(s) for the physiological parameter(s) is accurate. The data transformation process performed by the data processor is optionally used to remove artifacts from the input data to produce output data having higher accuracy than the input data and/or to extract information from the input data to generate output data estimating the values for physiological parameters that are not otherwise measured or reported using data from the sensor(s).

Mathematical and Computational Models

A mathematical model or a computer model, as used herein, involves the use of dependent state parameters and independent, variable, or constant model parameters in a mathematical representation of physiological processes that give rise to a physiological parameter being measured and processes through which sensor data is detected.

A mathematical model optionally includes model and/or state parameters that correspond directly to physiological parameters including vital signs, such as oxygen saturation of blood ($SpO_2$), heart rate (HR), respiratory rate (RR), and blood pressure (BP), which is optionally used to directly measure physiological parameters not traditionally directly measured with the aforementioned sensors, such as total blood volume (TBV), left-ventricular stroke volume (SV), vasomotor tone (VT), autonomous nervous system (ANS) tone, and stroke volume (SV); and hemoglobin-bound complexes, concentrations of metabolic intermediates, and concentrations of drugs present in one or more tissues or organs.

A mathematical model optionally also uses mathematical representations of physiological observations that do not correspond directly to any physiological process, such as mathematical representations of signals obtained from sensor data or empirically fitting a mathematical equation to data collected from a physiological source.

While the scope of a mathematical model cannot possibly encompass every single process of human physiology, it should have the capacity to interpret the measured observable(s). For instance, if the intent is to process electrocardiography (ECG) signals, a model describing the generation and propagation of electrical impulses in the heart should be included.

The fusion of two or more biomedical signals follows the same principle. For instance, if the intent is to measure blood pressure waves and electrocardiogram signals simultaneously, the use of a heart model describing both the electrical and mechanical aspects of the organ should be used. Initially, the model optionally also accepts manual data input as a complement to data from sensors. Non-limiting examples of manually entered data include food consumption over time, vital signs, gender, age, weight, and height.

Non-physiological models are optionally included in and/or coupled to the dynamic state-space model in cases where non-biomedical signals are measured. For instance, non-biomedical measurements are optionally used to enhance or complement biomedical measurements. A non-limiting example is the use of accelerometer data to enhance motion artifact rejection in biomedical measurements. In order to accomplish this, the physiological model is extended to describe both measurements, such as circulation: at rest, at different body postures (standing, supine, etc), and/or in motion, such as by using a force model relating accelerometer data to observed forces.

Dynamic State-Space Model

Figure 2:
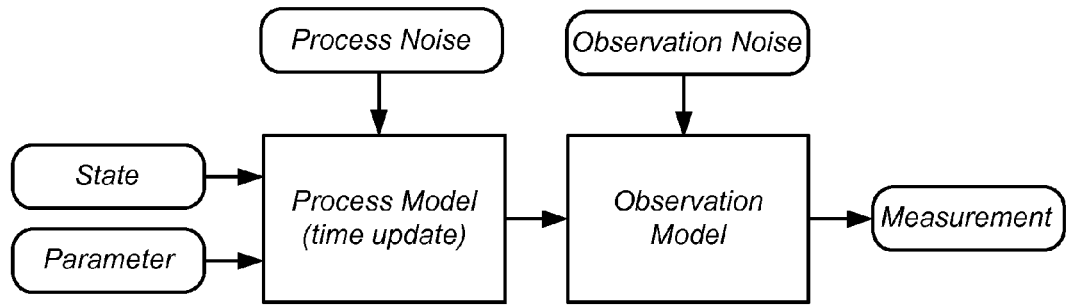
FIG. 2 is a flow chart showing inputs, outputs, and conceptual division of model parts for a dynamic state-space model (DSSM).
Figure 3:
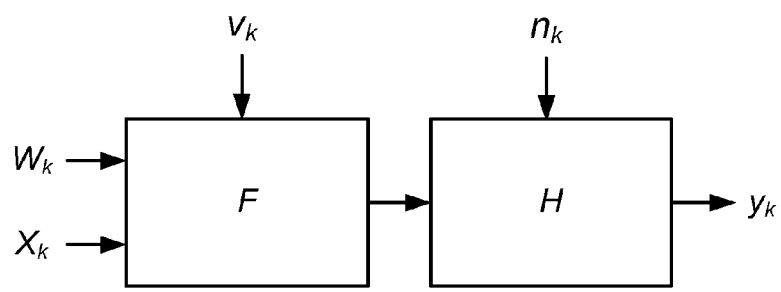
FIG. 3 is a block diagram showing mathematical representations of inputs, output and conceptual divisions of the DSSM shown in FIG. 2.

Referring now to FIG. 2 and FIG. 3, schematics of a dynamic state-space model (DSSM) used in the processing of data are provided. The dynamic state-space model includes a process model F that mathematically represents physiological processes involved in generating one or more physiological parameters measured by a biomedical sensor and describes the state of the subject over time in terms of state parameters. This mathematical model optimally includes mathematical representations accounting for process noise such as physiologically caused artifacts that may cause the sensor to produce a digital output that does not produce an accurate measurement for the physiological parameter being sensed. The dynamic state-space model also comprises an observational model H that mathematically represents processes involved in collecting sensor data measured by the biomedical sensor. This mathematical model optimally includes mathematical representations accounting for observation noise produced by the sensor apparatus that may cause the sensor to produce a digital output that does not produce an accurate measurement for a physiological parameter being sensed. Noise terms in the mathematical models are not required to be additive.

While the process and observational mathematical models are optionally conceptualized as separate models, they are preferably integrated into a single mathematical model that describes processes that produce a physiological parameter and processes involved in sensing the physiological parameter. That model, in turn, is integrated with a processing engine within an executable program stored in a data processor that is configured to receive digital data from one or more sensors and to output data to a display or other output formats.

FIG. 3 provides mathematical descriptions of the inputs and outputs corresponding to FIG. 2. Initially, values for state parameters, preferably in the form of a state vector $x_k$, are received by the dynamic state-space model together with input model parameters $W_k$. Process noise $v_k$ and observation noise $n_k$ are also received by the dynamic state-space model, which updates the state parameter vector and model parameter vector and produces an output observation vector $y_k$. Once the model is initialized, the updated state vector $x_{k+1}$, updated model parameters $W_{k+1}$, and time-specific sensor data are used as input for each calculation for subsequent iterations, or time steps.

The dynamic state-space model is integrated in a dual estimation processing engine or a joint estimation processing engine. The most favored embodiment makes use of a DSSM built into a Sigma point Kalman filter (SPKF) or Sequential Monte Carlo (SMC) processing engine. Sigma point Kalman filter (SPKF) refers to the collective name used for Kalman filters, which optionally do not use a derivative, that employ the deterministic sampling based sigma point approach to calculate approximations of the optimal terms of the Gaussian approximate linear Bayesian update rule, including unscented, central difference, square-root unscented, and square-root central difference Kalman filters.

SMC and SPKF processing engines operate on a general nonlinear dynamic state-space model having the form:

$$x_k = f(x_{k-1}, v_{k-1}; W) \quad (1)$$

$$y_k = h(x_k, n_k; W) \quad (2)$$

A hidden system state, $x_k$, propagates over time index, k, according to the system model, f. The process noise is $v_{k-1}$, and W is the vector of model parameters. Observations, $y_k$, about the hidden state are given by the observation model h and $n_k$ is the measurement noise. When W is fixed, only state estimation is required and either SMC or SPKF is optionally used to estimate the hidden states.

Unsupervised Machine Learning

Unsupervised machine learning, sometimes referred to as system identification or parameter estimation, involves determining the nonlinear mapping:

$$y_k = g(x_k; w_k) \quad (3)$$

where $x_k$ is the input, $y_k$ is the output, and the nonlinear map g(•) is parameterized by the model parameter vector W. The nonlinear map, for example, is optionally a feed-forward neural network, recurrent neural network, expectation maximization algorithm, or enhanced Kalman filter algorithm. Learning corresponds to estimating W in some about optimal fashion. In the preferred embodiment, SPKF or SMC is used for updating parameter estimates. One way to accomplish this is to write a new state-space representation $$w_{k+1} = w_k + r_k \quad (4)$$

$$d_k = g(x_k; w_k) + e_k \quad (5)$$

where $w_k$ correspond to a stationary process with identity state transition matrix, driven by process noise $r_k$. The desired output $d_k$ corresponds to a nonlinear observation on $w_k$.

Dual Estimation Engine for Estimation of State and Model Parameters

Figure 4:
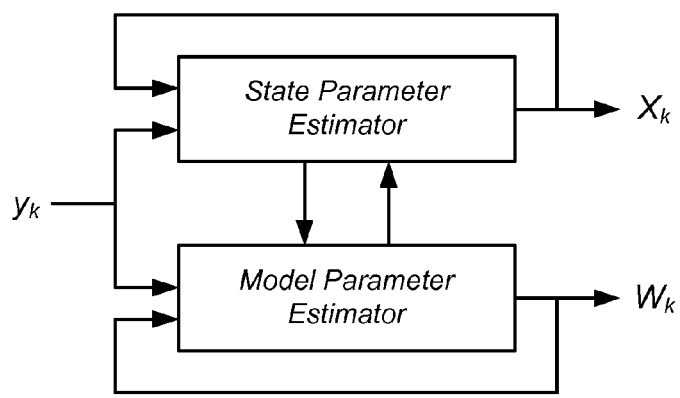
FIG. 4 is a mathematical representation of the process of dual estimation.
Figure 5:
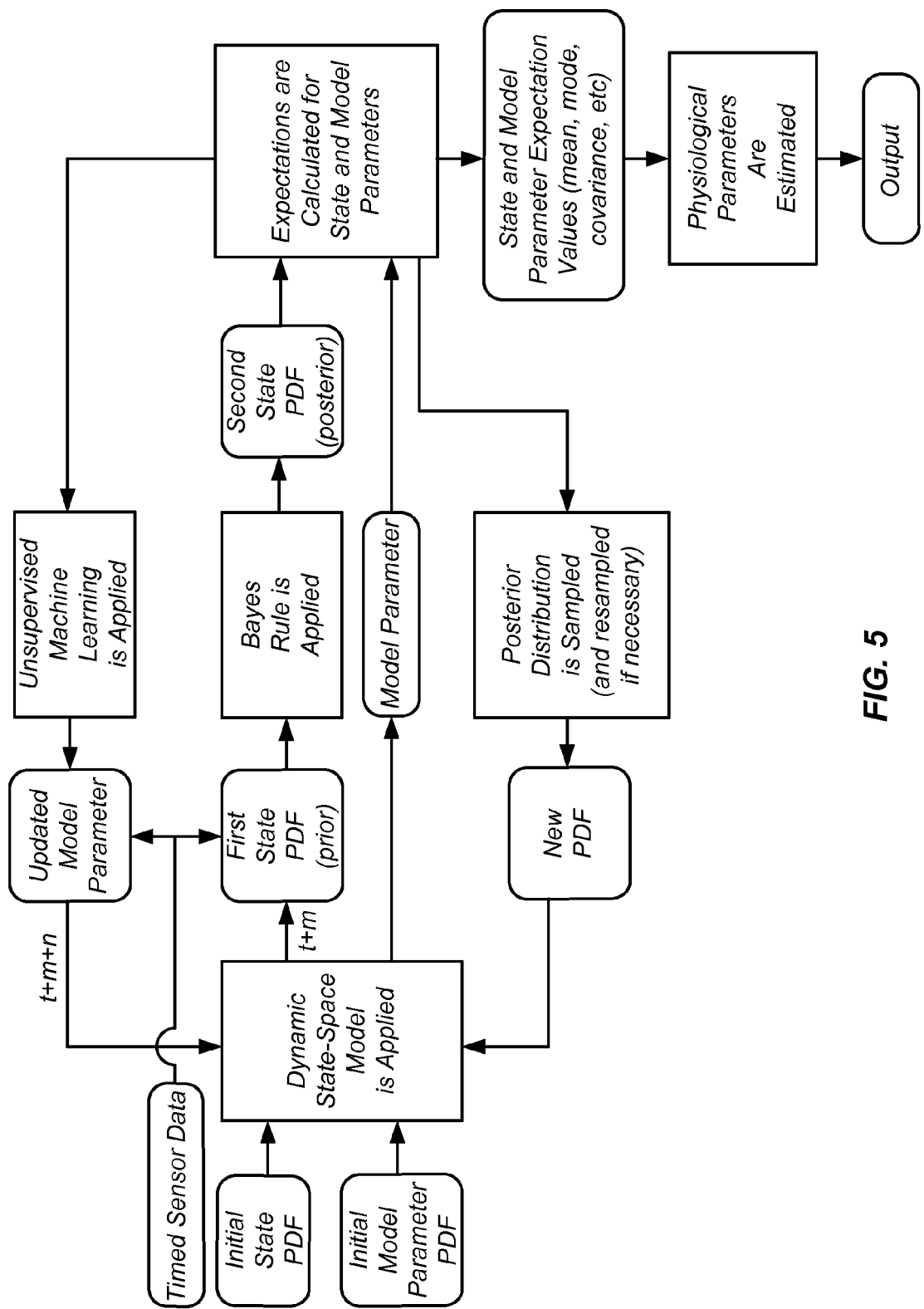
FIG. 5 is a schematic diagram showing the process steps involved in a dual estimation process.

Referring now to FIG. 4 and FIG. 5, the state and parameter estimation steps are optionally coupled in an iterative dual-estimation mode, such as by the process shown. This formulation for a state estimator operates on an adaptive dynamic state-space model. In the dual estimation process, states $x_k$ and parameters W are estimated sequentially inside a loop. When used in a data processor for a pulse oximeter, the current state $x_k$ from pulse oximeter sensor input $y_k$. States $x_k$, and parameters W are estimated sequentially inside a loop. Parameter estimates are passed from the previous iteration to state estimation for the current iteration. Several different implementations or variants of the SMC and SPKF methods exist, including the sigma-point, Gaussian-sum, and square-root forms. The particular choice may be influenced by the application.

The current estimate of the parameters $W_k$ is used in the state estimator as a given (known) input, and likewise the current estimate of the state $x_k$ is used in the parameter estimator. This results in a step-wise stochastic optimization within the combined state-parameter space.

The flow chart shown FIG. 5 provides a summary of the steps involved in dual estimation process. Initial probability distributions for state and model parameters are provided to the dynamic state-space model to produce an initial probability distribution function (PDF), which is also referred to herein as a first PDF or a prior PDF, representing the initial state. Data for a time $t_1$ from a sensor (new measurement) and the initial PDF are combined using a Bayesian statistical process to generate a second, posterior PDF that represents the state at the time of the measurement for the first sensor data. Expectation values for the second PDF are calculated, which may represent the most likely true value. Expectation values may also represent, for instance, the confidence interval or any statistical measure of uncertainty associated with the value. Based upon the expectation values, usually but not necessarily the values for state parameters having the highest probability of being correct, updated state parameters for time $t_1$ are combined with sensor data for time $t_1$ to update the model parameters for time $t_2$ in the dynamic state-space model by the process shown in FIG. 4. The expectation values are also fed into the dynamic state-space model as the state, in the form of a vector of state parameters (new PDF) as shown in FIG. 4. Once the state parameters and model parameters for the dynamic state-space model are updated to time $t_1$, the process is repeated with timed data for time $t_2$ to produce updated parameters for time $t_2$ and so forth. The time interval between time steps is usually constant such that time points may be described as t, t+n, t+2n, etc. If the time interval is not constant, then the time may be described using two or more time intervals as t, t+n, t+n+m, etc.

Joint Estimation Engine for Estimation of State and Model Parameters

Figure 6:
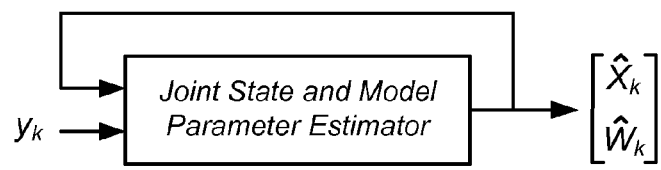
FIG. 6 is a mathematical representation of the process of joint estimation.
Figure 7:
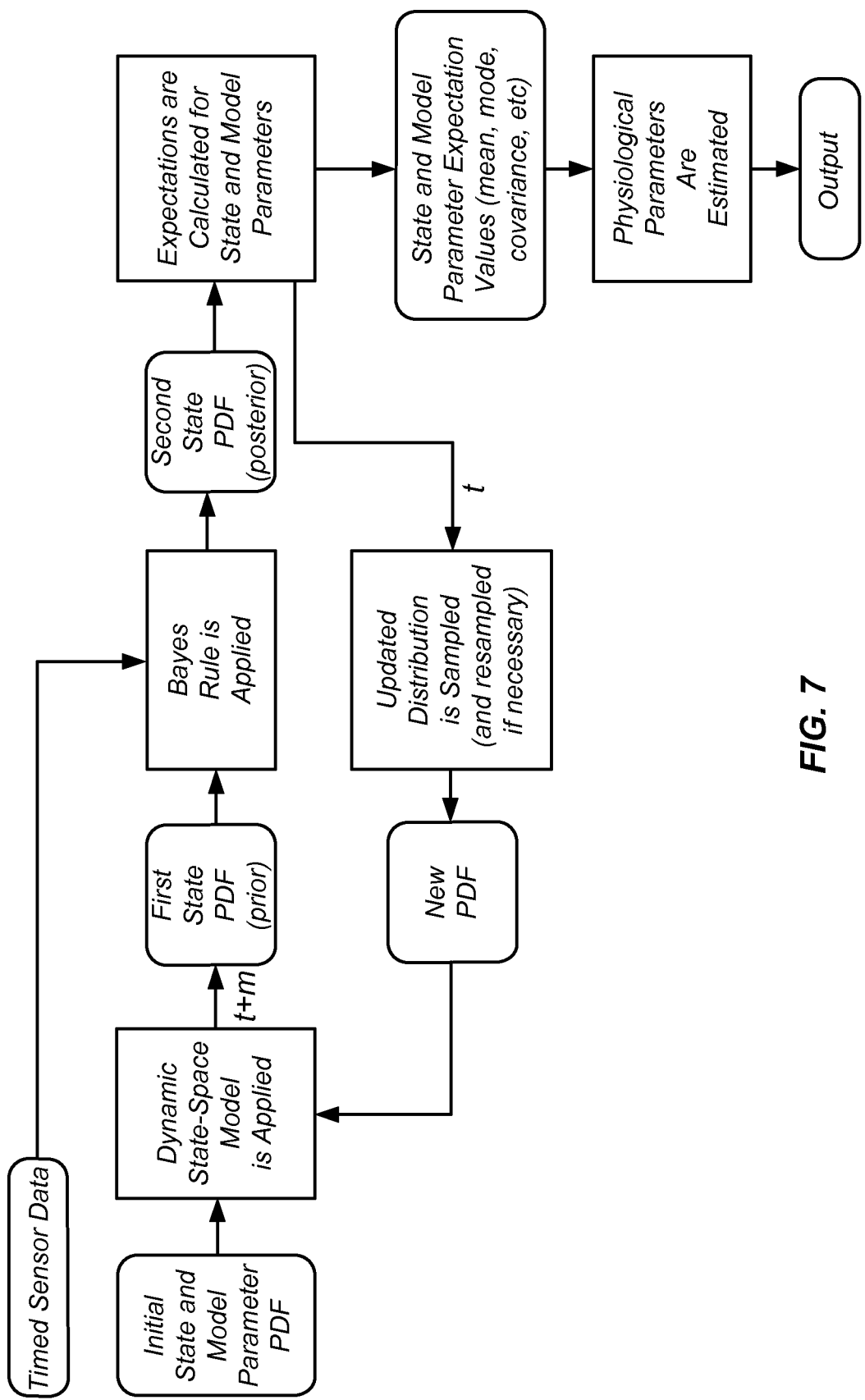
FIG. 7 is a schematic diagram showing the process steps involved in a joint estimation process.

Referring now to FIG. 6 and FIG. 7, the state and parameter estimation steps are optionally performed in a simultaneous joint-estimation mode as shown. The calculated variables for the state parameters and model parameters of the physiological model are concatenated into a single higher-dimensional joint state vector:

$$X = [x_k^T \ w_k^T]^T \quad (6)$$

where $x_k$ are the state parameters and $w_k$ the model parameters. The joint state space is used to produce simultaneous estimates of the states and parameters.

The flow chart shown FIG. 7 provides a summary of the steps involved in dual estimation process. The process is similar to that shown for dual estimation in FIG. 5, with the exception that model and state parameters are not separated into two separate vectors, but are represented together in a single vector. The process is initiated by entering a vector representing initial state and model parameter value distributions into the dynamic state-space model and producing an initial first PDF. The first PDF is combined with sensor data (new measurement) for time $t_1$ in a Bayesian statistical process to generate a second, posterior PDF that represents the state, and model parameters at time $t_1$. Expectation values for the second PDF are calculated, which may represent the most likely true value. Expectation values may also represent, for instance, the confidence interval or any statistical measure of uncertainty associated with the value. Based upon the expectation values, updated state and model parameters for time $t_1$ are entered into the dynamic state-space model by the process shown in FIG. 6. Once the state parameters and model parameters for the dynamic state-space model are updated to time $t_1$, the process is repeated with timed data for time $t_2$ to produce updated parameters for time $t_2$ and so forth.

Compared to dual estimation, both state and parameters are concatenated into a single vector that is transformed by the dynamic state-space model. Hence, no machine learning step is necessary in order to update model parameters. Joint estimation may be performed using a sequential Monte Carlo method or sigma-point Kalman method. These may take the form of unscented, central difference, square-root unscented, and square-root central difference forms. The optimal method will depend on the particular application.

Sequential Monte Carlo Methods

SMC methods estimate the probability distributions of all the model unknowns by propagating a large number of samples called probability particles in accordance with the system models (typically nonlinear, non-Gaussian, non-stationary) and the rules of probability. Artifacts are equivalent to noise with short-lived probability distributions, also called non-stationary distributions. The number of simulated particles scales linearly with computational power, with ≥100 particles being reasonable for real time processing with presently available processors. The system model describes pertinent physiology and the processor engine uses the system model as a "template" from which to calculate, using Bayesian statistics, posterior probability distribution functions (processed data). From this, the expectation values, such as the mean, and confidence intervals are optionally estimated, FIG. 7. The combination of SMC with Bayesian Statistics to calculate posterior probability distribution functions is often referred to as a Particle Filter.

SMC process nonlinear and non-Gaussian problems by discretizing the posterior into weighted samples, or probability particles, and evolving them using Monte Carlo simulation. For discretization, Monte Carlo simulation uses weighted particles to map integrals to discrete sums:

$$p(x_k \mid y_{1:k}) \approx \hat{p}(x_k \mid y_{1:k}) = \sum_{i=1}^n \delta(x_k - x_k^{(i)}) \quad (7)$$

where the random samples $\{x(i); i=1, 2, \ldots, N\}$, are drawn from $p(x_k|y_{1:k})$ and $\delta(.)$ is the Dirac delta function. Expectations of the form $$E[g(x_k)] = \int g(x_k) p(x_k|y_{1:k}) dx_k \quad (8)$$

are optionally approximated by the estimate:

$$E[g(x_k)] \approx \tilde{E}[g(x_k)] = \frac{1}{N} \sum_{i=1}^N g(x_k^{(i)}) \quad (9)$$

if the distribution has finite support. As N approaches infinity, the estimate converges to the true expectation.

The optimal Bayesian solution is outlined by the following recursive algorithm. Suppose the required PDF $p(x_{k-1}|y_{1:k-1})$ at time k−1 is available. In the prediction stage, the prior PDF at time k is obtained using the dynamic state-space model via the Chapman-Kolmogorov equation:

$$p(x_k|y_{1:k-1}) = \int p(x_k|y_{k-1})p(x_{k-1}|y_{1:k-1})dx_{k-1} \quad (10)$$

The dynamic state-space model model describing the state evolution $p(x_k|y_{k-1})$ is defined by the system equation (1) and the known statistics of $v_{k-1}$. At time step k a measurement $y_k$ becomes available, and this may be used to update the prior (updated stage) via Bayes' rule:

$$p(x_k|y_{1:k}) = \frac{p(y_k|x_k)p(x_k|y_{1:k-1})}{p(y_k|y_{1:k-1})} \quad (11)$$

where the normalizing constant $$p(x_k|y_{1:k-1}) = \int p(y_k|x_k)p(x_k|y_{1:k-1})dx_k \quad (12)$$

depends on the likelihood function $p(y_k|x_k)$ defined by the measurement model (equation 2) and the known statistics of $n_k$.

It is not possible to sample directly from the posterior density function so importance sampling from a known proposal distribution $\pi(x_{0:k}|y_{1:k})$ is used. One may use sigma-point Kalman filters, for example, to generate the proposal.

The known distribution is introduced into Equation 5 to yield:

$$E[g(x_{0:k})] = \int g(x_{0:k}) \frac{w_k(x_{0:k})}{p(y_{1:k})} \pi(x_{0:k}|y_{1:k})dx_{0:k} \quad (13)$$

where the variables $w_k(x_{0:k})$ are un-normalized importance weights, which are written as $w_k(x_{0:k})=w_k$:

$$w_k(x_{0:k}) = \frac{p(y_{1:k}|x_{0:k})p(x_{0:k})}{\pi(x_{0:k}|y_{1:k})} \quad (14)$$

resulting in a weighted expectation:

$$E[g(x_{0:k})] \approx \tilde{E}[g(x_{0:k})] = \sum_{i=1}^{N} \tilde{w}_k^{(i)} g(x_{0:k}^{(i)}) \quad (15)$$

where $\tilde{w}_k^{(i)}$ are normalized importance weights:

$$\tilde{w}_k^{(i)} = w_k^{(i)} / \sum_{j=1}^{N} w_k^{(j)} \quad (16)$$

Importance sampling is made sequential by reiterating the Markov 1$^{st}$ order assumption, resulting in the assumption that the current state is not dependent on future observations:

$$\pi(x_{0:k}|y_{1:k}) = \pi(x_{0:k-1}|y_{1:k-1})\pi(x_k|x_{0:k-1},y_{1:k}) \quad (17)$$

and that observations are conditionally independent given the states:

$$p(x_{0:k}) = p(x_0)\prod_{j=1}^{k} p(x_j|x_{j-1}) \quad (18)$$

$$p(y_{1:k}|x_{0:k}) = \prod_{j=1}^{k} p(y_j|x_j) \quad (19)$$

A recursive estimate for the importance weights is:

$$w_k = w_{k-1} \frac{p(y_k|x_k)p(x_k|x_{k-1})}{\pi(x_k|x_{0:k-1},y_{1:k})} \quad (20)$$

which is called Sequential Importance Sampling (SIS). SIS suffers from degeneracy so that, over a few iterations, all but one of the importance weights will be zero, effectively removing a large number of samples. To remedy this, samples with low importance weights may be eliminated while high importance samples may be multiplied. One way to accomplish this is Sampling-Importance Resampling (SIR), which involves mapping the Dirac random measure $$\{x_k^{(i)}, \tilde{w}_k^{(i)}; i=1,\ldots,N\} \quad (21)$$

into a measure with equal weights, 1/N:

$$\left\{x_k^{(j)}, \frac{1}{N}; i=1,\ldots,N\right\} \quad (22)$$

A pseudo-code for a generic SMC (also called bootstrap filter or condensation algorithm) is written as:
1. Importance sampling step. For i=1, ..., N, do:
   i) sample $x_k^{(i)} \sim p(x_k|x_{k-1}^{(i)})$
   ii) evaluate $w_k^{(i)} \sim w_{k-1}^{(i)} p(y_k|x_k^{(i)})$
   iii) normalize $\tilde{w}_k^{(i)} = w_k^{(i)} / \sum_{j=1}^{N} w_k^{(j)}$
2. Importance resampling step
   $x_k^{(i)}, \tilde{w}_k^{(i)}$
   i) eliminate or multiply samples according to weights to obtain N random samples approximately distributed according to $p(x_k|y_{1:k})$.
   ii) For i=1, ..., N, set $w_k^{(i)} = \tilde{w}_k^{(i)} = N^{-1}$
3. Output
   i) any expectation, for instance:

$$\hat{x}_k = E[x_k|y_{1:k}] \approx \frac{1}{N}\sum_{i=1}^{N} x_k^{(i)}$$

SPKF may be used to approximate probability distributions. Assuming that x has a mean $\bar{x}$, covariance $P_x$, and dimension L, a set of 2L+1 weighted sigma-points, $S_i = \{w_i, X_i\}$, is chosen according to:

$$X_0 = \bar{x} \qquad w_0^{(m)} = \frac{h^2 - L}{h^2} \quad (23)$$

$$X_i = \bar{x} + (h\sqrt{P_x})_i, \; i=1,\ldots,L \qquad w_i^{(m)} = \frac{1}{2h^2} \quad i=1,\ldots,2L$$

$$X_i = \bar{x} - (h\sqrt{P_x})_i, \; i=L+1,\ldots,2L \qquad w_i^{(o1)} = \frac{1}{4h^2} \quad i=1,\ldots,2L$$

$$w_i^{(o1)} = \frac{h^2-1}{4h^4} \quad i=1,\ldots,2L$$

where h is a scaling parameter. Each sigma-point is propagated through the dynamic state-space model to yield the posterior sigma-point set, $Y_i$:

$$Y_i = h(f(X_i)), i=0,\ldots,2L \quad (24)$$

From this, the posterior statistics are calculated using a procedure resembling the linear Kalman filter. For instance, for the unscented Kalman filter case, a SPKF variant, the time-update equations are:

$$X_{k|k-1}^x = f(X_{k-1}^x, X_{k-1}^x, u_{k-1}) \qquad (25)$$

$$\hat{x}_k^- = \sum_{i=0}^{2L} w_i^{(m)} X_{i,k|k-1}^x \qquad (26)$$

$$P_{x_k}^- = \sum_{i=0}^{2L} w_i^{(o)} (X_{i,k|k-1}^x - \hat{x}_k^-)(X_{i,k|k-1}^x - \hat{x}_k^-)^T \qquad (27)$$

and the measurement-update equations are:

$$Y_{k|k-1} = h(X_{k|k-1}^x - X_{k-1}^x) \qquad (28)$$

$$\hat{y}_k^- = \sum_{i=n}^{2L} w_i^{(m)} Y_{i,k|k-1} \qquad (29)$$

$$P_{\tilde{y}_k} = \sum_{i=0}^{2L} w_i^{(o)} (Y_{i,k|k-1} - \hat{y}_k^-)(Y_{i,k|k-1} - \hat{y}_k^-)^T \qquad (30)$$

$$P_{x_k y_k} = \sum_{i=0}^{2L} w_i^{(o)} (X_{i,k|k-1}^x - \hat{x}_k^-)(Y_{i,k|k-1} - \hat{y}_k^-)^T \qquad (31)$$

$$K_k = P_{x_k y_k} P_{\tilde{y}_k}^{-1} \qquad (32)$$

$$\hat{x}_k = \hat{x}_k^- + K_k(y_k - \hat{y}_k^-) \qquad (33)$$

$$P_{x_k} = P_{x_k}^- - K_k P_{\tilde{y}_k} K_k^T \qquad (34)$$

where x, v and n superscripts denote the state, process noise and measurement noise dimensions, respectively.

The mathematical structure for sequential Monte Carlo and SPKF represent two examples of a family of probabilistic inference methods exploiting Monte Carlo simulation and the sigma point transform, respectively, in conjunction with a Bayesian statistical process.

SPKF and sequential Monte Carlo (SMC) are recent developments in probabilistic inference. Like SMC, SPKF evolve the state using the full nonlinear dynamic state-space model, but represent probability distributions using a sigma-point set. This is a deterministic step that replaces the stochastic Monte Carlo step in the SMC. As a result, SPKF lose accuracy when posterior distributions depart heavily from the Gaussian form, such as with bimodal or heavily-tailed distributions, or with strong nonstationary distributions such as those caused by motion artifacts in pulse oximeters. For these cases SMC are more suitable.

SPKF yields higher-order accuracy than the extended Kalman filter (EKF) and its related variants with equal algorithm complexity, $O(L^2)$. SPKF returns $2^{nd}$ order accuracy for non-linear and non-Gaussian problems, and $3^{rd}$ order for Gaussian problems. EKF has only $1^{st}$ order accuracy for nonlinear problems. Both EKF and SPKF approximate state distributions with Gaussian random variables (GRV). However, the EKF propagates the GRV using a single measure (usually the mean) and the $1^{st}$ order Taylor expansion of the nonlinear system. The SPKF, on the other hand, decomposes the GRV into distribution moments (sigma points) and propagates those using the unmodified nonlinear system. SPKF implementation is simpler than EKF since it optionally does not use a derivative. That is, it uses the unmodified dynamic state-space model form, and therefore does not require lengthy Jacobian derivations.

The data processing method is also capable of prediction because the method is configurable to operate faster than real time measurements. At any given time during data processing, the measurement PDF, obtained either from SPKF or SMC, embodies all available statistical information up to that point in time. It is therefore possible to march the system model forwards in time, for instance, using the same sequential Monte Carlo method, to obtain deterministic or stochastic simulations of future signal trajectories. In this way, the future health status (physiological state) of a patient is optionally predicted with attached probabilities indicating the confidence of each prediction.

Noise Adaptation

The data processing method may benefit from a noise adaptation method if timed sensor data contains noise and/or artifact that changes its spectral qualities over time. That is, has a non-stationary probability distribution function. Here, a known algorithm such as the Robins-Monro or Annealing methods may be added to the data processing method in order to adapt the probability distribution functions of noise terms (stochastic terms) in the dynamic state-space model according to changing noise and artifact present in sensor data.

Output

In general, the output may include estimates of the true measured signals (i.e. processed data), and estimates of values for one or more physiological parameters measured by one or more sensors from which data was received, and estimates of values for one or more physiological parameters not measured by the sensors from which data was received (data extraction). A state parameter estimate is the processed data from the physiological sensor. Both noise and artifacts are optionally attenuated and/or rejected even though they may have very distinct probability distribution functions and may mimic the real signal. A model parameter estimate may be also used to produce a physiological parameter. For example, an estimate of total blood volume may be used to diagnose hemorrhage or hypovolemia; an estimate of tissue oxygen saturation may indicate poor tissue perfusion and/or hypoxia; estimates of glucose uptake in several tissues may differentiate between diabetes mellitus types and severities; and estimates of carotid artery radius may be indicative of carotid artery stenosis.

EXAMPLES

Pulse Oximeter with Probabilistic Data Processing

Figure 8:
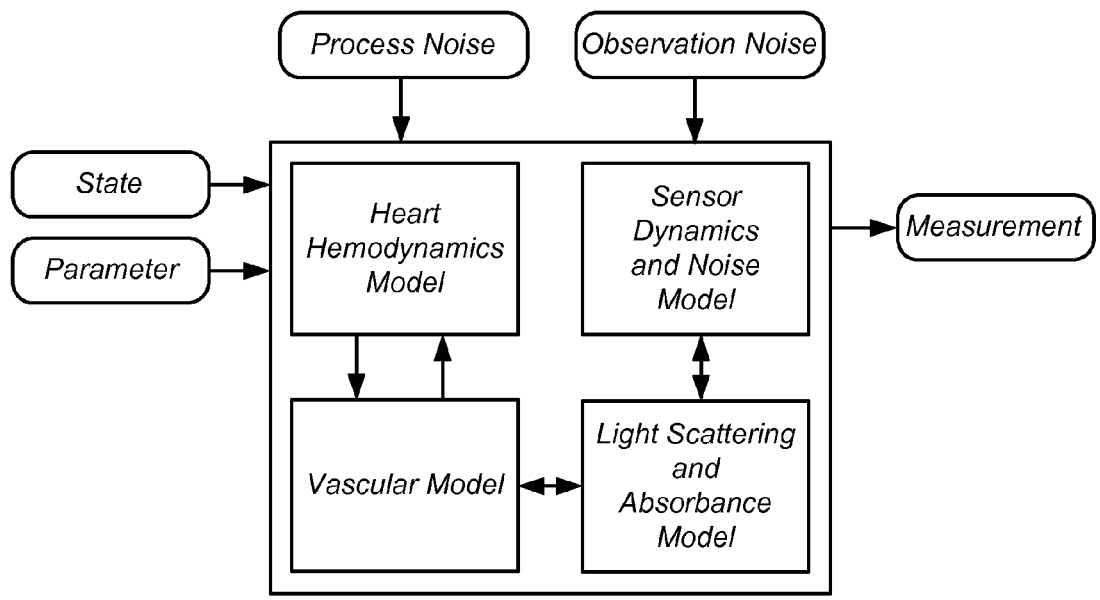
FIG. 8 is a flow chart showing the components of a DSSM used for pulse oximetry data processing.
Figure 9:
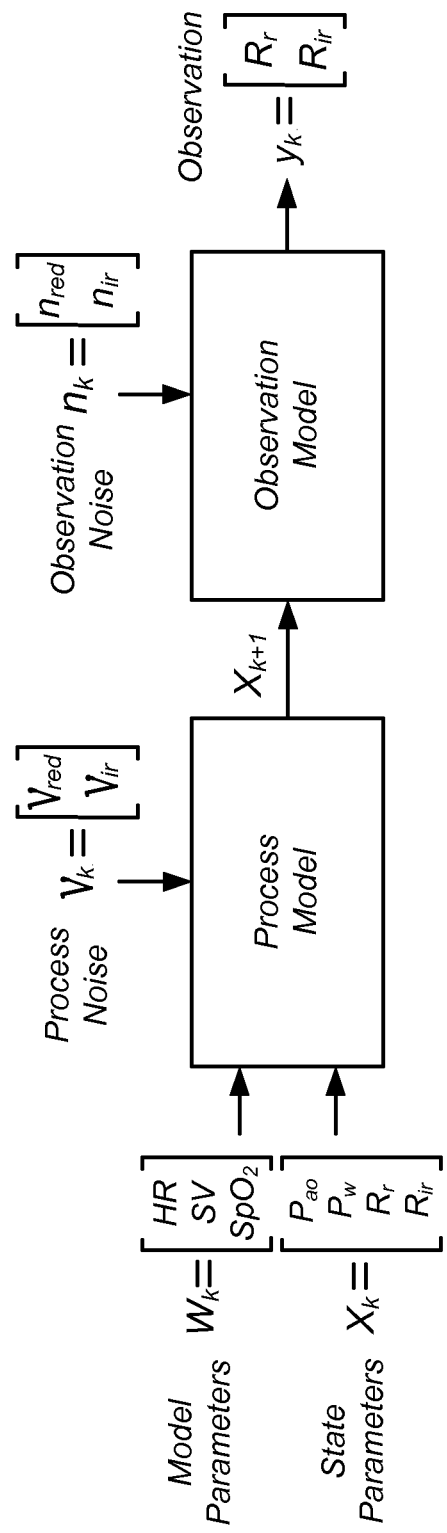
FIG. 9 is a flow chart showing examples of parameter inputs and outputs for a DSSM used for pulse oximetry data processing.

Referring now to FIG. 8, the components of a dynamic state-space model suitable for processing data from a pulse oximeter model, including components required to describe processes occurring in a subject, are shown. Referring now to FIG. 9, the dynamic state-space model broken down into process and observation models, and including all input and output variables is shown. Heart rate (HR), stroke volume (SV) and whole-blood oxygen saturation ($SpO_2$) are estimated from input noisy red and infrared intensity ratios (R). Radial (Pw) and aortic (Pao) pressures are also available as state estimates.

In this example, the dynamic state-space model comprises the following function to represent cardiac $$Q_{CO}(t) = \overline{Q}_{CO} \sum_{k=1}^{5} a_k \exp\left[\frac{-(t-b_k)^2}{c_k^2}\right] \qquad (31)$$

wherein cardiac output Qco(t), is expressed as a function of heart rate (HR) and stroke volume (SV) and where $Q_{co}$=(HR× SV)/60. The cardiac output function pumps blood into a Windkessel 3-element model of the vascular system including two state variables: aortic pressure, Pao, and radial (Windkessel) pressure, Pw:

$$P_{w,k+1} = \frac{1}{C_w R_p}((R_p + Z_o)Q_{CO} - P_{co,k}) \cdot \delta t + P_{w,k} \quad (32)$$

$$P_{co,k+1} = P_{w,k+1} + Z_o Q_{CO} \quad (33)$$

Rp and Zo are the peripheral resistance and characteristic aortic impedance, respectively. The sum of these two terms is the total peripheral resistance due to viscous (Poiseuille-like) dissipation:

$$Z_o = \sqrt{\rho/AC_1} \quad (34)$$

where ρ is blood density. The elastic component due to vessel compliance is a nonlinear function including thoracic aortic cross-sectional area, A:

$$A(P_{co}) = A_{max}\left[\frac{1}{2} + \frac{1}{\pi}\arctan\left(\frac{P_{co} - P_0}{P_1}\right)\right] \quad (35)$$

where Amax, $P_0$ and $P_1$ are fitting constants correlated with age and gender:

$$A_{max} = (5.62 - 1.5(\text{gender})) \cdot \text{cm}^2 \quad (36)$$

$$P_0 = (76 - 4(\text{gender}) - 0.89(\text{age})) \cdot \text{mmHg} \quad (37)$$

$$P_1 = (57 - 0.44(\text{age})) \cdot \text{mmHg} \quad (38)$$

The time-varying Windkessel compliance, Cw, and the aortic compliance per unit length, Cl, are:

$$C_w = lC_l = l\frac{dA}{dP_{co}} = l\frac{A_{max}/(\pi P_1)}{1 + \left(\frac{P_{co} - P_0}{P_1}\right)^2} \quad (39)$$

where l is the aortic effective length. The peripheral resistance is defined as the ratio of average pressure to average flow. A set-point pressure, Pset, and the instantaneous flow:

$$R_p = \frac{P_{set}}{(HR \cdot SV)/60} \quad (40)$$

are used to provide compensation autonomic nervous system responses. The value for Pset is adjusted manually to obtain 120 over 75 mmHg for a healthy individual at rest. The compliance of blood vessels changes the interactions between light and tissues with pulse. This is accounted for using a homogenous photon diffusion theory for a reflectance or transmittance pulse oximeter configuration. For the reflectance case:

$$R = \frac{I_{ac}}{I_{dc}} = \frac{\Delta I}{I} = \frac{3}{2}\Sigma'_a K(\alpha, d, r)\Sigma_a^{art}\Delta V_a \quad (41)$$

for each wavelength. In this example, the red and infrared bands are centered at ~660 nm and ~880 nm. I denotes the detected intensities: total reflected (no subscript), and the pulsating (ac) and background (dc) components. Va is the arterial blood volume, which changes as the cross-sectional area of illuminated blood vessels, $\Delta A_w$, changes as:

$$\Delta V_a \approx r \cdot \Delta A_w \quad (42)$$

where r is the source-detector distance. The tissue scattering coefficient, $\Sigma_s'$, is assumed constant but the arterial absorption coefficient, $\Sigma a^{art}$, depends on blood oxygen saturation, $SpO_2$:

$$\Sigma_a^{art} = \frac{H}{v_i}[SpO_2 \cdot \sigma_a^{100\%} + (1 - SpO_2) \cdot \sigma_a^{0\%}] \quad (43)$$

which is the Beer-Lambert absorption coefficient, with hematocrit, H, and red blood cell volume, $v_i$. The optical absorption cross sections for red blood cells containing totally oxygenated ($HbO_2$) and totally deoxygenated (Hb) hemoglobin are $\sigma_a^{100\%}$ and $\sigma_a^{0\%}$, respectively.

The function K(α,d,r) contains, along with the scattering coefficient, the wavelength, sensor geometry and oxygen saturation dependencies that alter the effective optical pathlengths:

$$K(\alpha, d, r) \approx \frac{-r^2}{1 + \alpha r} \quad (44)$$

The attenuation coefficient α is:

$$\alpha = \sqrt{3\Sigma_a(\Sigma_s + \Sigma_a)} \quad (45)$$

where $\Sigma_a$ and $\Sigma_s$ are whole-tissue absorption and scattering coefficients, respectively, which are calculated from Mie Theory.

Red and infrared K values as a function of $SpO_2$ may be represented by two linear fits:

$$\overline{K}_r \approx -4.03 \cdot SpO_2 - 1.17 \quad (46)$$

$$\overline{K}_{ir} \approx 0.102 \cdot SpO_2 - 0.753 \quad (47)$$

in mm². The overbar denotes the linear fit of the original function. The pulsatile behavior of $\Delta Aw$, which couples optical detection with the cardiovascular system model, is:

$$\Delta A_w = \frac{A_{w,max}}{\pi} \frac{P_{w,1}}{P_{w,1}^2 + (P_{w,k+1} - P_{w,0})^2}\Delta P_w \quad (48)$$

with $P_{w,0} = (\frac{1}{3})P_0$ and $P_{w,1} = (\frac{1}{3})P_1$ to account for the poorer compliance of arterioles and capillaries relative to the thoracic aorta. Third and fourth state variables, the red and infrared reflected intensity ratios, $R = I_{ac}/I_{dc}$, are:

$$R_{r,k+1} = c\Sigma'_{x,r}\overline{K}_r\Sigma_{a,r}^{art}\Delta A_w + R_{r,k} + v_r \quad (49)$$

$$R_{ir,k+1} = c\Sigma'_{s,ir}\overline{K}_{ir}\Sigma_{a,ir}^{art}\Delta A_w + R_{ir,k} + v_{ir} \quad (50)$$

Here, v are Gaussian-distributed process noises intended to capture the baseline wander of the two channels. The constant c subsumes all factors common to both wavelengths and is treated as a calibration constant. The observation model adds Gaussian-distributed noises, n, to $R_r$ and $R_{ir}$:

$$\begin{bmatrix} y_{r,k} \\ y_{ir,k} \end{bmatrix} = \begin{bmatrix} R_{r,k} \\ R_{ir,k} \end{bmatrix} + \begin{bmatrix} n_{r,k} \\ n_{ir,k} \end{bmatrix} \quad (51)$$

Figure 11A:
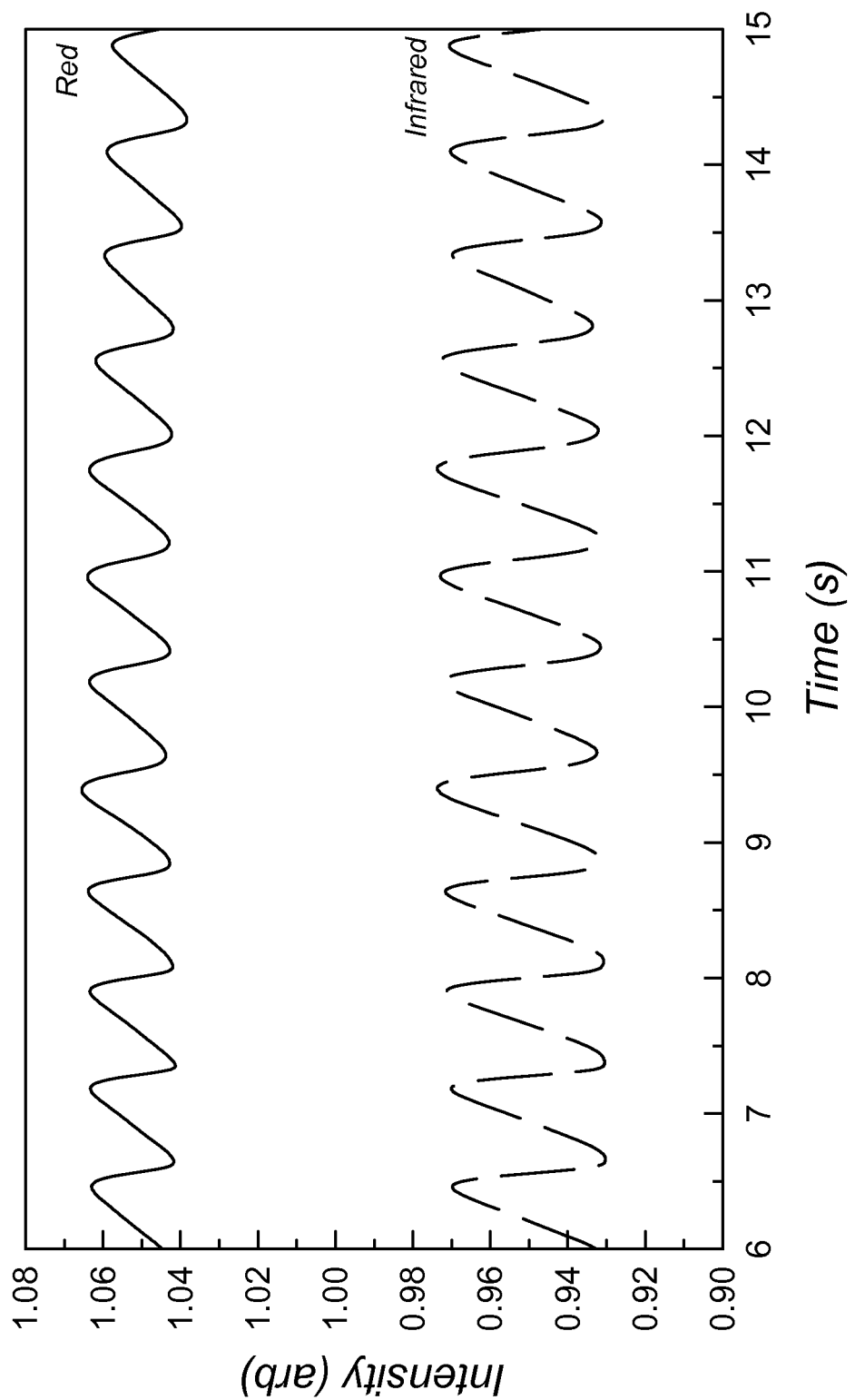
FIG. 11 is a chart showing input sensor data, FIG. 11A, and processed output data of heart rate, FIG. 11B, stroke volume, FIG. 11C, cardiac output, FIG. 11D, oxygen, FIG. 11E, and pressure, FIG. 11F, from a data processor configured to process pulse oximetry data.
Figure 11B:
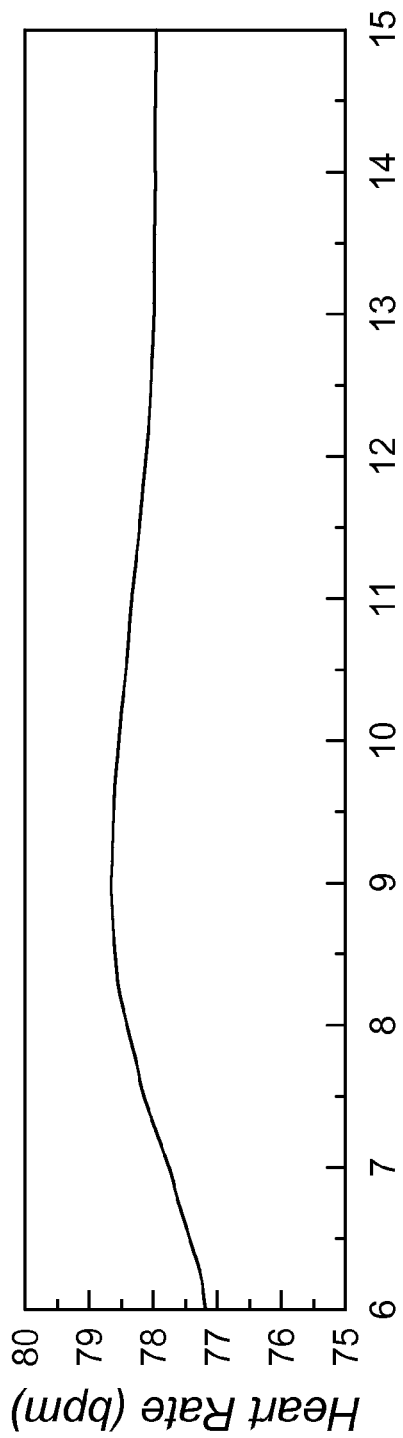
Figure 11C:
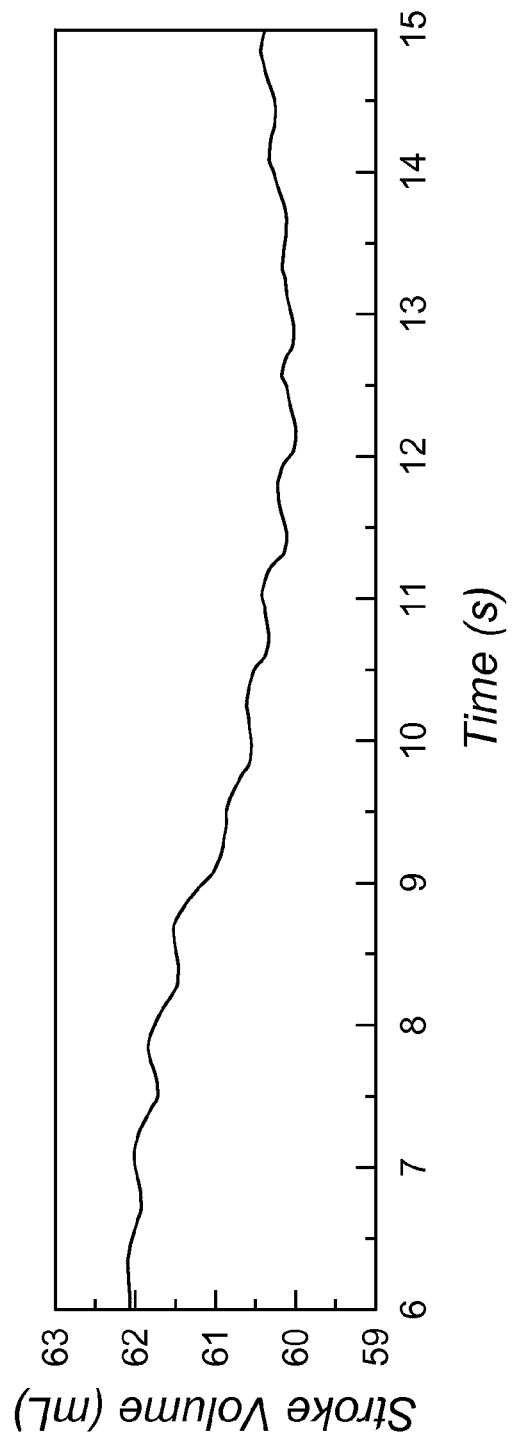
Figure 11D:
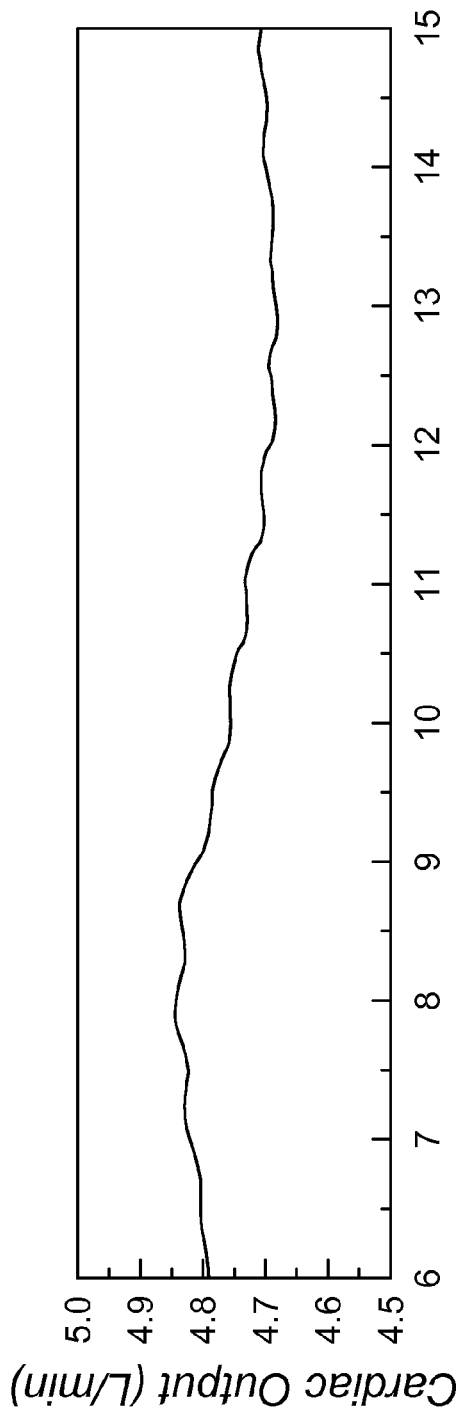
Figure 11E:
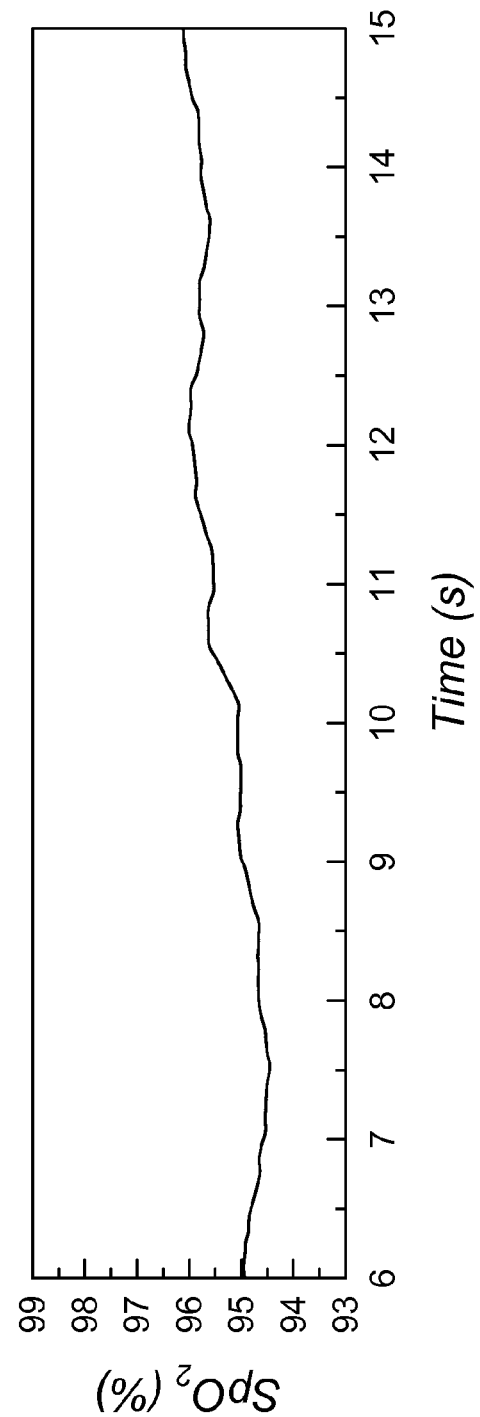
Figure 11F:
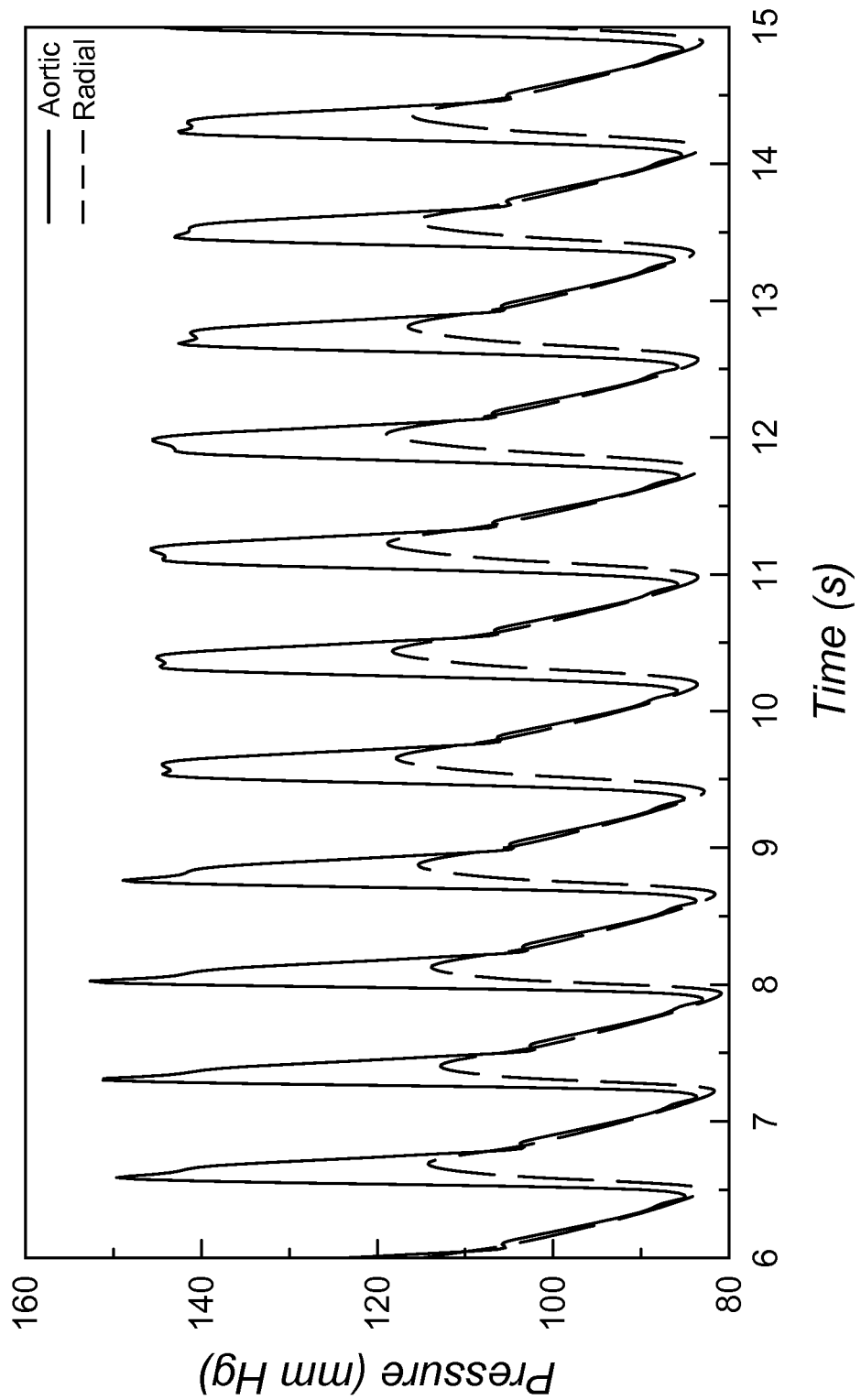
Figure 12A:
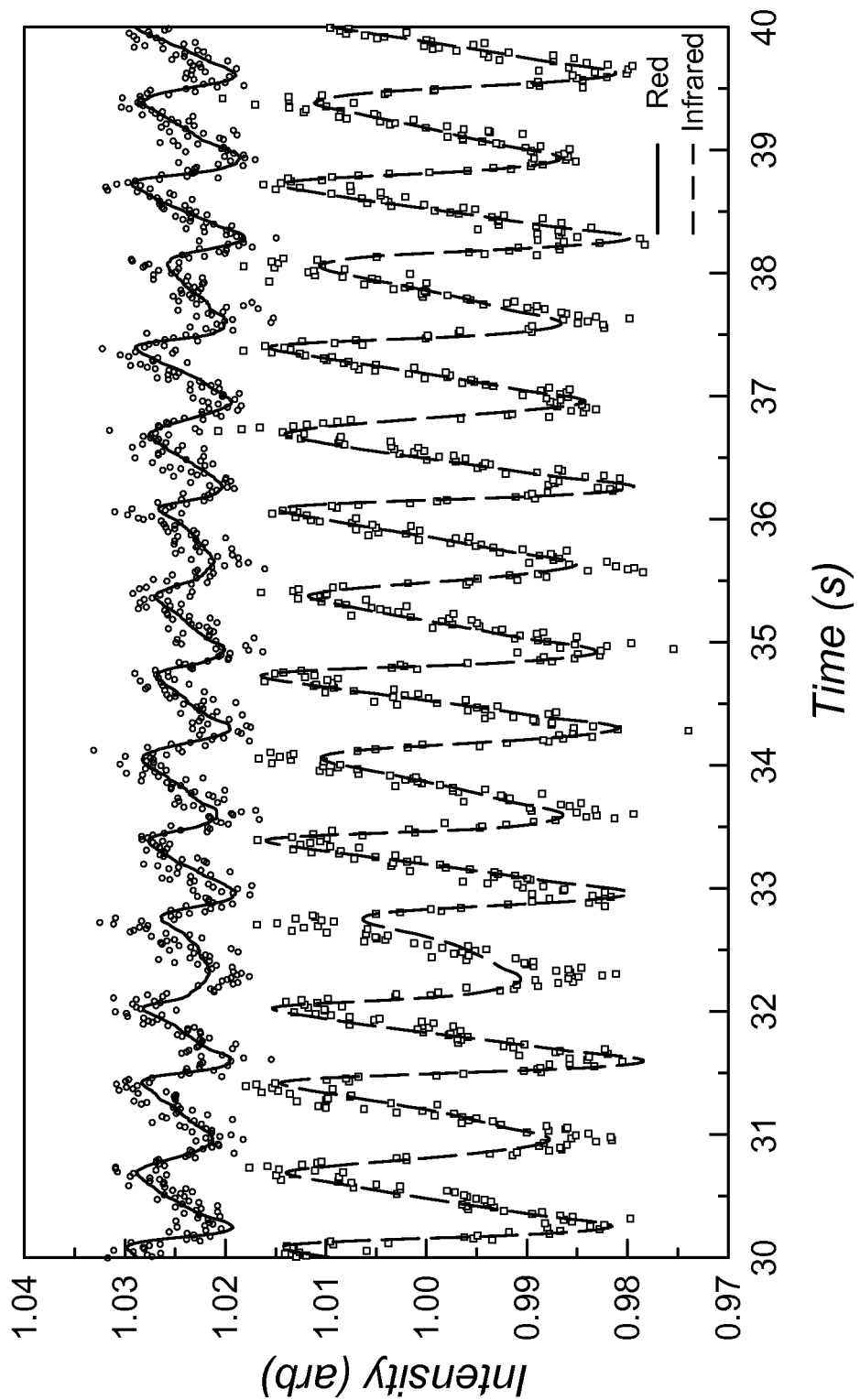
FIG. 12 is a chart showing input sensor data, FIG. 12A, and processed output data, FIGS. 12A-12E, from a data processor configured to process pulse oximetry data under a low blood perfusion condition.
Figure 12B:
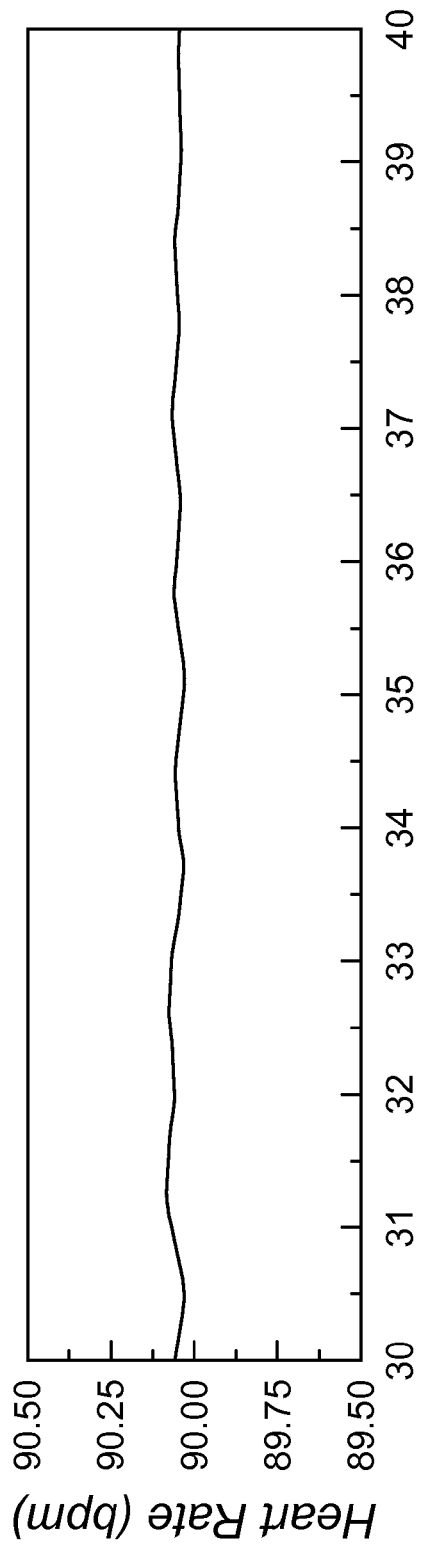
Figure 12C:
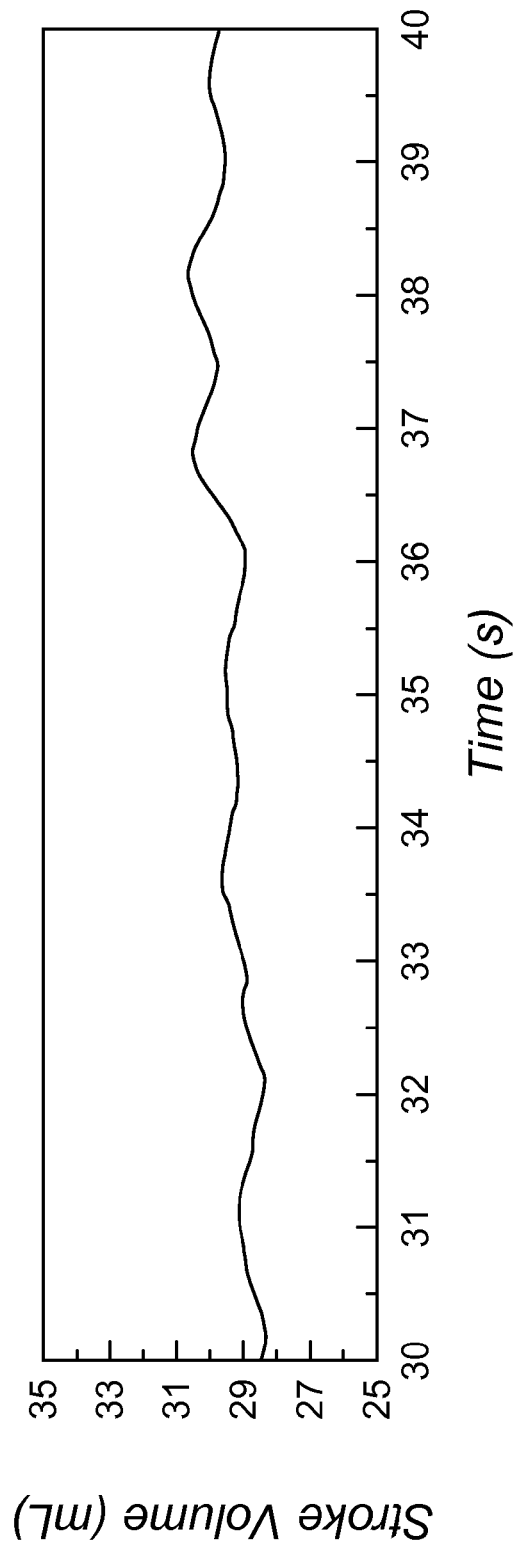
Figure 12D:
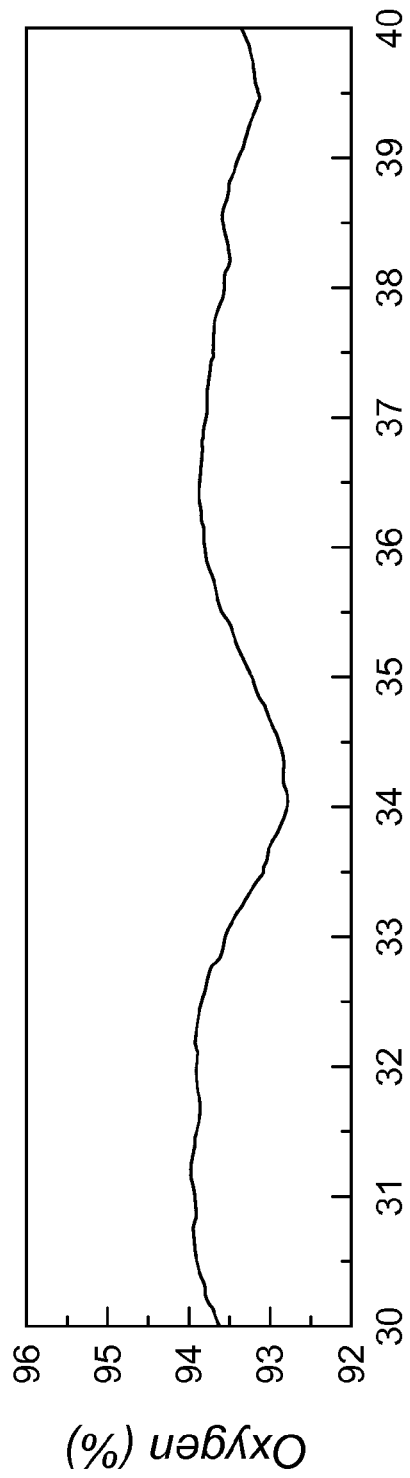
Figure 12E:
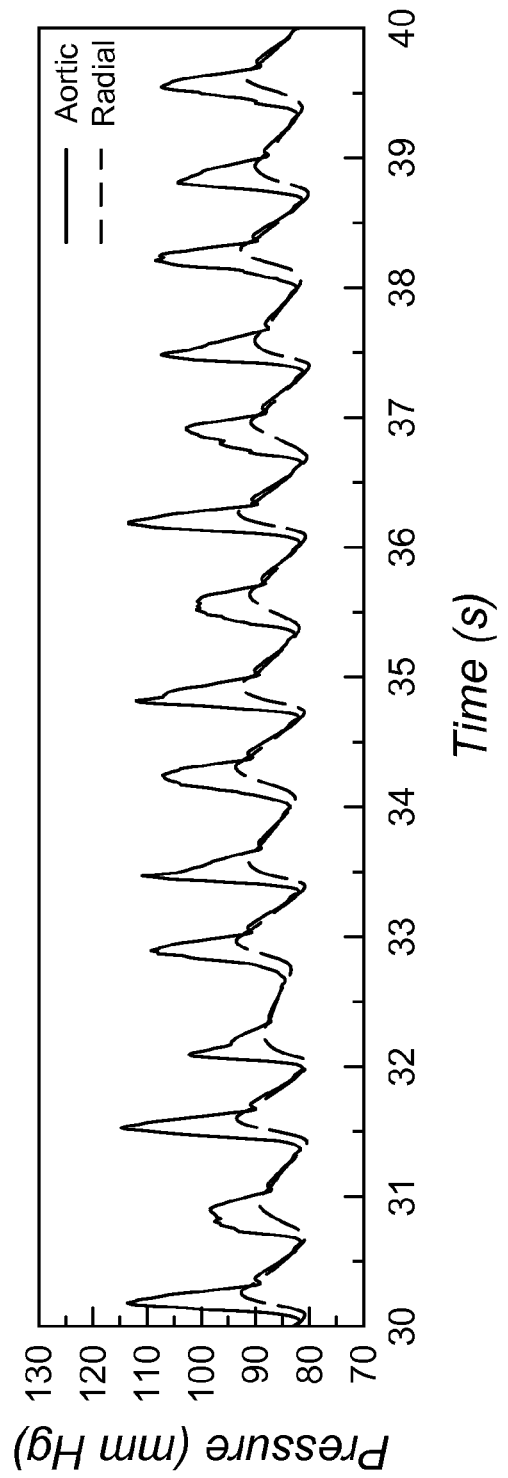

A calibration constant c was used to match the variance of the real Iac/Idc signal with the variance of the dynamic state-space model generated signal for each wavelength. After calibration, the age and gender of the patient was entered. Estimates for the means and covariances of both state and parameter PDFs were entered. Referring now to FIG. 11, estimates for a 15 second stretch of data is provided. Photoplethysmographic waveforms (FIG. 11A) were used to extract heart rate (FIG. 11B), left-ventricular stroke volume (FIG. 11C), cardiac output (FIG. 11D), blood oxygen saturation (FIG. 11E), and aortic and systemic (radial) pressure waveforms (FIG. 11F). Results of processing pulse oximetry at low blood perfusion are shown in FIG. 12. Low signal-to-noise photoplethysmographic waveforms (FIG. 12A) were used to extract heart rate (FIG. 12B), left-ventricular stroke volume (FIG. 12C), blood oxygen saturation (FIG. 12D), and aortic and systemic (radial) pressure waveforms (FIG. 12E).

Electrocardiograph with Probabilistic Data Processing

Figure 10:
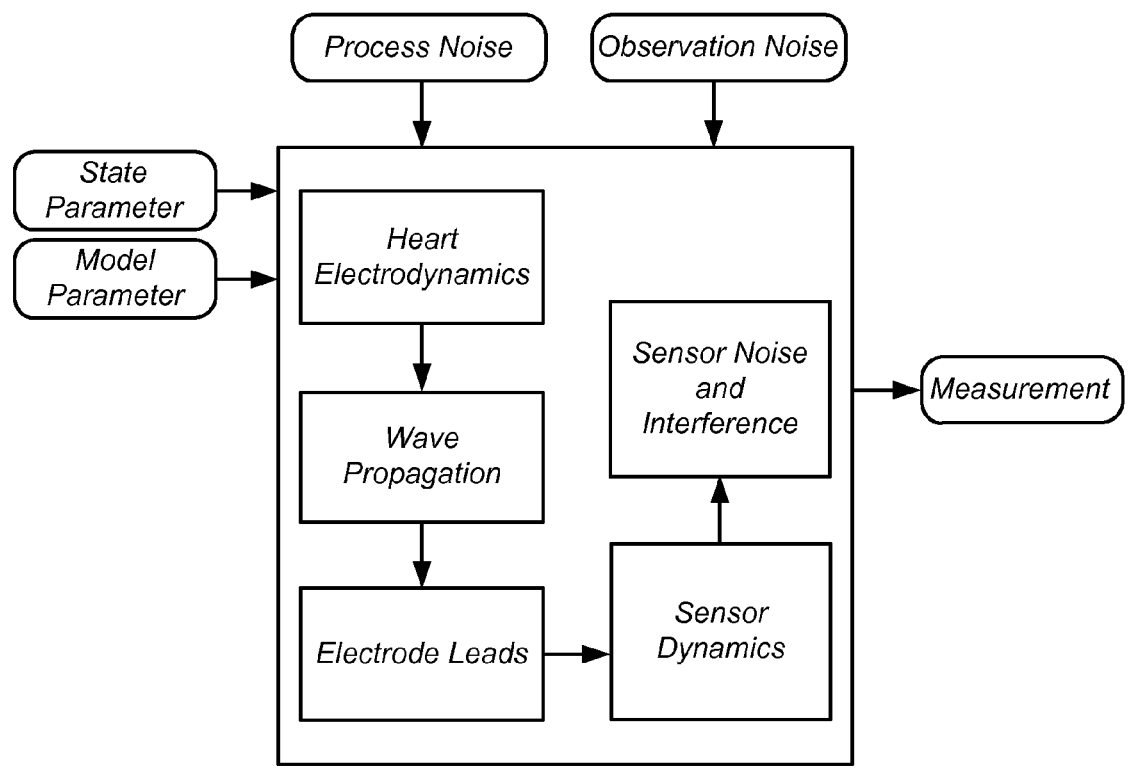
FIG. 10 is a flow chart showing the components of a DSSM used for electrocardiography data processing.

FIG. 10 is a schematic of a dynamic state-space model suitable for processing electrocardiograph data, including components required to describe the processes occurring in a subject. The combination of SPKF or SMC in state, joint or dual estimation modes is optionally used to filter electrocardiography (ECG) data. Any physiology model adequately describing the ECG signal can be used, as well as any model of noise and artifact sources interfering or contaminating the signal. One non-limiting example of such a model is a model using a sum of Gaussians with amplitude, center and standard deviation, respectively, for each wave (P, Q, R, S, T−, T+15) in an ECG. The observation model comprises the state plus additive Gaussian noise, but more realistic pink noise or any other noise distributions can be used.

Figure 13A:
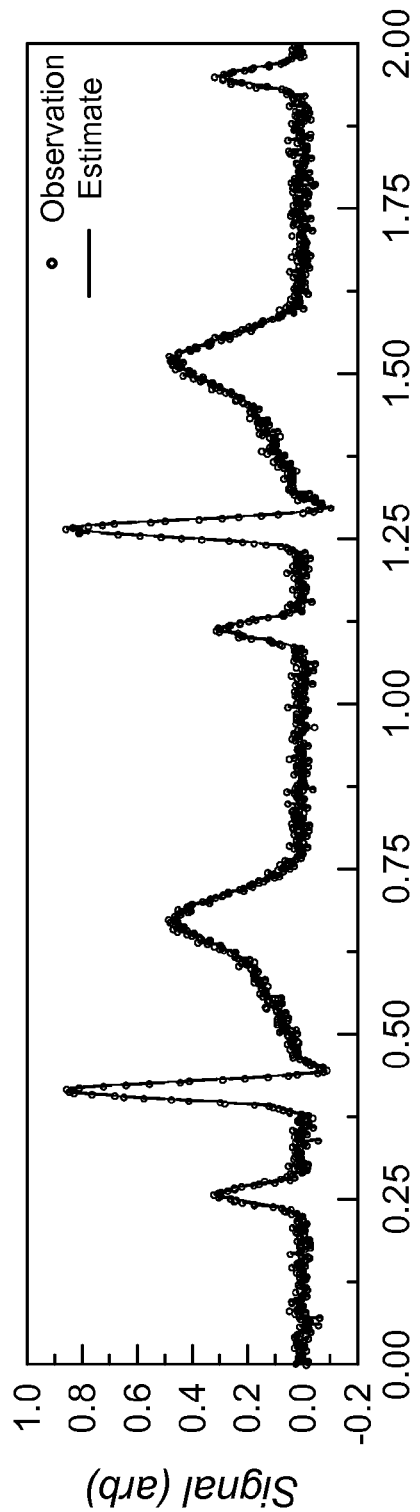
FIG. 13 is a chart showing noisy non-stationary ECG sensor data input, FIG. 13A and FIG. 13B and processed heart rate and ECG output, FIG. 13A and FIG. 13 B, for a data processor configured to process ECG sensor data.
Figure 13B:
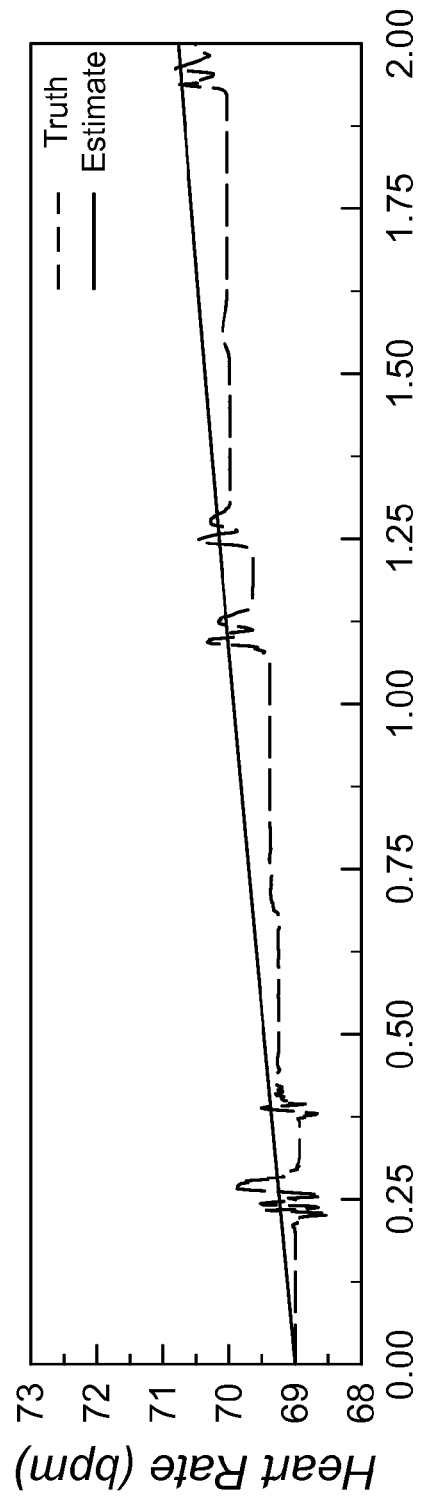
Figure 14A:
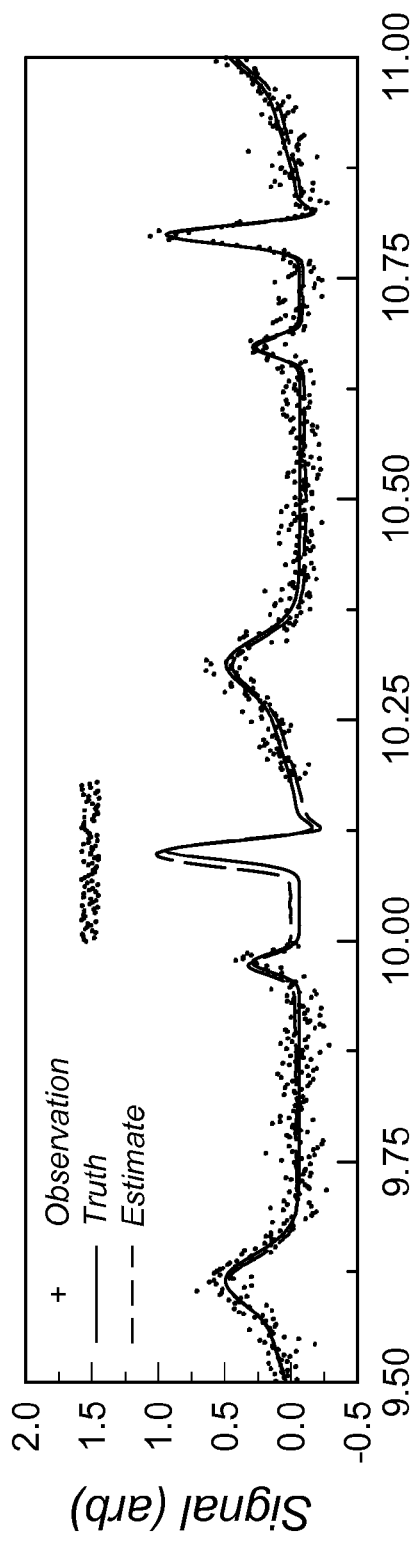
FIG. 14A and FIG. 14B are charts showing input ECG sensor data and comparing output data from a data processor according to the present invention with output data generating using a Savitzky-Golay FIR data processing algorithm.
Figure 14B:
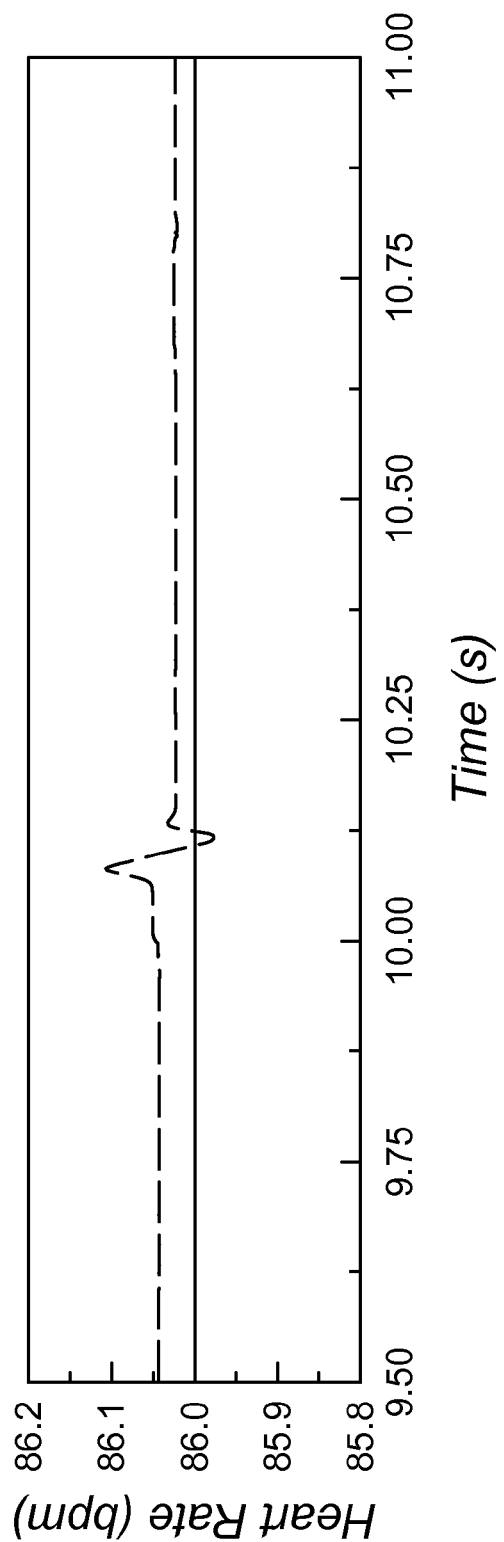

Referring now to FIGS. 13A and 13B, the results of processing a noisy non-stationary ECG signal are shown. Heart rate oscillations representative of normal respiratory sinus arrhythmia are present in the ECG. The processor accomplishes accurate, simultaneous estimation of the true ECG signal and heart rate that follows closely the true values. Referring now to FIGS. 14A and 14B, the performance of the processor in a noise and artifact-corrupted signal is shown. A clean ECG signal representing one heart beat (truth) was contaminated with additive noise and an artifact in the form of a plateau at R and S peaks (beginning at time=10 sec). Estimates by the processor remain close to the true signal despite the noise and artifact.

The above description describes an apparatus for generation of a physiological estimate of a physiological process of an individual from input data, where the apparatus includes a biomedical monitoring device having a data processor configured to run a dual estimation algorithm, where the biomedical monitoring device is configured to produce the input data, and where the input data comprises at least one of: a photoplethysmogram; and an electrocardiogram. The dual estimation algorithm is configured to use a dynamic state-space model to operate on the input data using both an iterative state estimator and an iterative model parameter estimator in generation of the physiological estimate, where the dynamic state-space model is configured to mathematically represent probabilities of physiological processes that generate the physiological estimate and mathematically represent probabilities of physical processes that affect collection of the input data. Generally, the algorithm is implemented using a data processor, such as in a computer, operable in or in conjunction with a biomedical monitoring device.

In yet another embodiment, the method, system, and/or apparatus using a probabilistic model to extract physiological information from a biomedical sensor, described supra, optionally uses a sensor providing time-dependent signals. More particularly, pulse ox and ECG examples were provided, infra, to describe the use of the probabilistic model approach. However, the probabilistic model approach is more widely applicable.

Some examples of physiological sensors used for input into the system with a corresponding physiological model include:
 an ECG having 2 to 12 leads yielding an ECG waveform used to determine an RR-interval and/or various morphological features related to arrhythmias;
 pulse photoplethysmography yielding a PPG waveform for determination of hemoglobins and/or total hemoglobin;
 capnography or IR absorption yielding a real time waveform for carbon dioxide determination, end-tidal $CO_2$, an inspired minimum, and/or respiration rate;
 a temperature sensor for continuous determination of core body temperature and/or skin temperature;
 an anesthetic gas including $N_2O$, $CO_2$ used to determine minimum alveolar concentration of an inhaled anesthetic;
 a heart catheter yielding a thermodilution curve for determination of cardiac index and/or blood temperature;
 an impedance cardiography sensor yielding a thoracic electrical bioimpedance reading for determination of thoracic fluid content, accelerated cardiac index, stroke volume, cardiac output, systemic vascular resistance;
 a mixed venous oxygen saturation catheter for determination of $SvO_2$;
 an electroencephalogram (EEG) yielding an EEG waveform and characteristics thereof, such as spectral edge frequency, mean dominant frequency, peak power frequency, compressed spectral array analysis—color pattern display, delta-theta-alpha-beta band powers, any of which are used for cardiac functions described herein;
 electromyography (EMG) yielding an EMG waveform including frequency measures, event detection, and/or amplitude of contraction;
 auscultation yielding sound pressure waveforms;
 transcutaneous blood gas sensors for determination of $CO_2$ and $O_2$;
 a pressure cuff yielding a pressure waveform for determination of systolic pressure, diastolic pressure, mean arterial pressure, heart rate, and/or hemodynamics;
 spirometry combining capnography and flow waveforms for information on respiratory rate, tidal volume, minute volume, positive end-expiratory pressure, peak inspiratory pressure, dynamic compliance, and/or airway resistance;
 fetal and/or maternal sensors, such as ECG and sound (auscultatory) sensors for determination of fetal movement, heart rate, uterine activity, and/or maternal ECG;
 laser Doppler flowmetry yielding a velocity waveform for capillary blood flow rate;
 an ultrasound and/or Doppler ultrasound yielding a waveform, such as a 2D or 3D image, for occlusion of blood vessel walls, blood flow velocity profile, and other body site dependent measures;
 a perspirometer yielding a continuous or semi-continuous surface impedance for information on skin perspiration levels; and a digital medical history database to calibrate the model or to screen the database for patient diseases and/or conditions.

Some examples of non-physiological sensors used for input into the system with a corresponding physiological model include:
 an accelerometer;
 a three axes accelerometer;
 a gyroscope;
 a compass;
 light;
 a GPS;
 a microphone; and
 an ambient temperature sensor.

While a specific dynamic state-space models and input and output parameters are provided for the purpose of describing the present method, the present invention is not limited to the dynamic state-space models, sensors, biological monitoring devices, inputs, outputs.

Although, the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for generating a physiological estimate from input data, comprising the steps of:
   generating input data using a biomedical monitoring device comprising a data processor configured to run a dual estimation algorithm, wherein the input data comprises at least one of:
   a photoplethysmogram; and
   an electrocardiogram,
   processing said input data using said dual estimation algorithm, said dual estimation algorithm configured to use a dynamic state-space model to operate on the input data using both an iterative state estimator and an iterative model parameter estimator in generation of said physiological estimate, said dynamic state-space model configured to: mathematically represent probabilities of physiological processes that generate said physiological estimate and mathematically represent probabilities of physical processes that affect collection of the input data;
   said state estimator iteratively:
      operating on an initial input probability distribution function or a re-sampled probability distribution function using said dynamic state-space model to generate a second probability distribution function;
      applying Bayes rule to said second probability distribution function and the input data to form a third probability distribution function; and
      re-sampling said third probability distribution function as said re-sampled probability distribution function;
   generating said physiological estimate using said model parameter estimator, said physiological estimate comprising:
      a blood oxygen saturation; and
      a left-ventricular stroke volume; and
   warning of a hemorrhage using said physiological estimate.

2. The method of claim 1, further comprising the step of:
   said dynamic state-space model processing said second probability distribution function using a sequential Monte Carlo algorithm.

3. The method of claim 2, further comprising the steps of said model parameter estimator iteratively:
   providing an initial model parameter or providing an updated model parameter as an input to said dynamic state-space model to generate a current value for said physiological estimate;
   using said third probability function and said current model parameter to form an expectation model; and
   combining said expectation model with the input data using unsupervised machine learning to generate said updated model parameter.

4. The method of claim 3, further providing an age input and a gender input in generation of said expectation model.

5. The method of claim 3, wherein said expectation model comprises a confidence interval representing an accuracy probability of said current model parameter.

6. The method of claim 1, further comprising the step of:
   combining into the input data at least two of:
      said plethysmogram;
      said electrocardiogram; and
      blood pressure monitor data.

* * * * *